(12) United States Patent
Ling

(10) Patent No.: US 11,318,110 B2
(45) Date of Patent: *May 3, 2022

(54) PHARMACEUTICAL COMPOSITION FOR REDUCING LOCAL FAT AND USES THEREOF

(71) Applicant: Caliway Biopharmaceuticals Co., Ltd., New Taipei (TW)

(72) Inventor: Yu-Fang Ling, New Taipei (TW)

(73) Assignee: Caliway Biopharmaceuticals Co., Ltd., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/749,347

(22) Filed: Jan. 22, 2020

(65) Prior Publication Data

US 2020/0197324 A1   Jun. 25, 2020

Related U.S. Application Data

(63) Continuation-in-part of application No. 15/754,429, filed as application No. PCT/IB2016/055102 on Aug. 26, 2016, now Pat. No. 10,610,496, which is a continuation of application No. PCT/CN2015/088340, filed on Aug. 28, 2015.

(60) Provisional application No. 62/299,702, filed on Feb. 25, 2016, provisional application No. 62/257,846, filed on Nov. 20, 2015.

(51) Int. Cl.
| | | |
|---|---|---|
| *A61K 31/12* | (2006.01) | |
| *A61K 9/107* | (2006.01) | |
| *A61K 31/353* | (2006.01) | |
| *A61P 3/06* | (2006.01) | |
| *A61K 31/7048* | (2006.01) | |
| *A61K 31/05* | (2006.01) | |
| *A61K 45/06* | (2006.01) | |
| *A61K 31/135* | (2006.01) | |

(52) U.S. Cl.
CPC .............. *A61K 31/12* (2013.01); *A61K 9/107* (2013.01); *A61K 31/05* (2013.01); *A61K 31/135* (2013.01); *A61K 31/353* (2013.01); *A61K 31/7048* (2013.01); *A61K 45/06* (2013.01); *A61P 3/06* (2018.01)

(58) Field of Classification Search
CPC ...... A61K 31/12; A61K 9/107; A61K 31/353; A61K 31/7048; A61K 31/05; A61K 45/06; A61K 31/135; A61K 9/1075; A61K 9/0019; A61P 3/06
See application file for complete search history.

(56) References Cited

U.S. PATENT DOCUMENTS

| | | |
|---|---|---|
| 6,383,482 B1 | 5/2002 | Gorsek |
| 6,475,530 B1 | 11/2002 | Kuhrts |
| 7,923,026 B2 | 4/2011 | Moschwitzer |
| 7,977,319 B1 | 7/2011 | Levine |
| 9,458,086 B1 | 10/2016 | Patel et al. |
| 10,610,496 B2 | 4/2020 | Ling |
| 2001/0021703 A1 | 9/2001 | Kosak |
| 2003/0147979 A1 | 8/2003 | Mae et al. |
| 2004/0071799 A1 | 4/2004 | Xu et al. |
| 2004/0146539 A1 | 7/2004 | Gupta |
| 2005/0267221 A1 | 12/2005 | Wellen |
| 2006/0121158 A1 | 6/2006 | Ferruzzi et al. |
| 2006/0188590 A1 | 8/2006 | Ono |
| 2009/0047371 A1 | 2/2009 | Turini et al. |
| 2009/0324703 A1 | 12/2009 | Frautschy et al. |
| 2010/0048887 A1 | 2/2010 | Anderson et al. |
| 2010/0129304 A1 | 5/2010 | Ahlnas |
| 2010/0316679 A1 | 12/2010 | Sinclair et al. |
| 2011/0009496 A1 | 1/2011 | Lunsmann et al. |
| 2011/0151103 A1 | 6/2011 | Gore |
| 2011/0281957 A1 | 11/2011 | Kuhrts |
| 2012/0088829 A1 | 4/2012 | Berl |
| 2012/0177623 A1 | 7/2012 | Naghavi et al. |
| 2013/0096143 A1 | 4/2013 | Falla et al. |
| 2013/0202572 A1 | 8/2013 | Hastings |
| 2013/0245118 A1 | 9/2013 | Kuhrts |
| 2013/0273175 A1 | 10/2013 | Finley |
| 2014/0141082 A1 | 5/2014 | Song |
| 2014/0348961 A1 | 11/2014 | Shimada et al. |
| 2015/0306165 A1 | 10/2015 | Ling et al. |
| 2016/0287533 A1 | 10/2016 | Banerjee et al. |
| 2017/0157195 A1 | 6/2017 | Ling et al. |
| 2018/0243211 A1 | 8/2018 | Ling |

(Continued)

FOREIGN PATENT DOCUMENTS

| | | |
|---|---|---|
| CN | 1812764 A | 8/2006 |
| CN | 101095665 A | 1/2008 |
| CN | 101310718 A | 11/2008 |

(Continued)

OTHER PUBLICATIONS

[No Author Listed], Fat Burning Needle. Lofter.com May 23, 2017. Accessible at lofter.com/tag/%E7%87%83%E8%84%82%E9%. 7 pages.

(Continued)

*Primary Examiner* — Sahar Javanmard

(74) *Attorney, Agent, or Firm* — McDermott Will & Emery LLP

(57) ABSTRACT

The present invention provides a pharmaceutical composition for reducing localized fat, comprising drug-containing micelles made of surfactants, and curcumin encapsulated in said drug-containing micelles. This pharmaceutical composition for reducing localized fat can reduce the fat at the administration site, and has the advantages of high stability, high bioavailability for fat tissue, few side effects, and sustained release.

19 Claims, 17 Drawing Sheets

(56) References Cited

U.S. PATENT DOCUMENTS

2020/0163906 A1    5/2020   Ling et al.
2020/0338152 A1    10/2020   Ling

FOREIGN PATENT DOCUMENTS

| | | |
|---|---|---|
| CN | 101632655 A | 1/2010 |
| CN | 102106816 A | 6/2011 |
| CN | 102357226 A | 2/2012 |
| CN | 103285401 A | 9/2013 |
| EP | 1077211 A2 | 2/2001 |
| EP | 1582204 A2 | 10/2005 |
| EP | 3187189 A1 | 7/2017 |
| JP | 2007-063137 A | 3/2007 |
| JP | 2007-131603 A | 5/2007 |
| JP | 2011-132151 A | 7/2011 |
| TW | 200427416 A | 12/2004 |
| TW | 201201794 A | 1/2012 |
| TW | 201540294 A | 1/2015 |
| TW | 201707685 A | 3/2017 |
| WO | 2006/087759 A2 | 8/2006 |
| WO | 2007/041276 A2 | 4/2007 |
| WO | 2007/112996 A2 | 10/2007 |
| WO | 2009/066303 A2 | 5/2009 |
| WO | 2009/158248 A2 | 12/2009 |
| WO | 2010/048114 A1 | 4/2010 |
| WO | 2010/062824 A2 | 6/2010 |
| WO | 2010/106191 A1 | 9/2010 |
| WO | 2014/138426 A2 | 9/2014 |
| WO | 2015/081319 A2 | 6/2015 |
| WO | 2016/029870 A1 | 3/2016 |
| WO | WO 2017/037593 A2 | 3/2017 |

OTHER PUBLICATIONS

[No Author Listed], Kolliphor ELP | Macrogolglycerol ricinoleate Ph. Eur., Polyoxyl-35-castor oil USP/NF. BASF The Chemical Company. Mar. 2012. 4 pages.

[No Author Listed], Kolliphor RH 40 | Macrogolglycerolhydroxystearat Ph. Eur., Polyoxyl-40 Hydrogenated castor oil USP/NF. BASF The Chemical Company. Dec. 2011. 6 pages.

[No Author Listed], Lipolysis needle how to dissolved fat pin to lose weight myth. 39 Health Network. Jan. 1, 2015. Accessible at read01.com/kDAMky.html. 9 pages.

[No Author Listed], Quercetin—Increases Fat Metabolism and Fat Burning | Muscular Development. Written by Team MD. Jan. 14, 2014. Accessible at musculardevelopment.com/articles/fat-loss/12555-dietar. 2 pages.

[No Author Listed], Synephrine—Fat Burner Ingredient Profile. May 23, 2017. Accessible at youbutslimmer.com/synephrine-weight-loss-uk. 5 pages.

Cadena et al., Nanoencapsulation of quercetin and resveratrol into elastic liposomes. Biochim Biophys Acta. Feb. 2013;1828(2):309-16. doi: 10.1016/j.bbamem.2012.10.022. Epub Oct. 25, 2012.

Chen et al., Targeted delivery of curcumin to tumors via PEG-derivatized FTS-based micellar system. AAPS J. May 2014;16(3):600-8. doi: 10.1208/s12248-014-9595-6. Epub Apr. 5, 2014.

Cherniack, Polyphenols: planting the seeds of treatment for the metabolic syndrome. Nutrition. Jun. 2011;27(6):617-23. doi: 10.1016/j.nut.2010.10.013. Epub Mar. 2, 2011. Abstract Only.

Davis et al., The dietary flavonoid quercetin increases VO(2max) and endurance capacity. Int J Sport Nutr Exerc Metab. Feb. 2010;20(1):56-62. doi: 10.1123/ijsnem.20.1.56.

Dong et al., Effects of Curcuma Longa MeOH Extract on Adipogenesis and Lipolysis in 3T3-L1 Adipocycles. J Korean Soc Food Sci Nutr. 2009;11:347.

Hong et al., Several varieties of injections state with surfactantss quality specification and safety. Chinese J Experimental Traditional Medical Formulae. Jan. 2010;16(1):115-9.

Hu et al., Enhancement of Oral Bioavailability of Curcumin by a Novel Solid Dispersion System. AAPS PharmSciTech. Dec. 2015;16(6):1327-34. doi: 10.1208/s12249-014-0254-0. Epub Mar. 25, 2015.

Inchai et al., Investigation On Solubility And Stability Of Curcumin In Aqueous Polysorbate Micelle. Int J Adv Sci Eng and Technol. IJASEAT Oct. 2015;3(4):157-61.

Jannin et al., Formulation of a self-emulsifying lipid formulation of curcumin. AAPS Annual Meeting and Exposition. Nov. 2014. Poster R6159. doi: 10.13140/RG.2.231621.24809. 1 page.

Kang et al., Curcumin decreases oleic acid-induced lipid accumulation via AMPK phosphorylation in hepatocarcinoma cells. Eur Rev Med Pharmacol Sci. Oct. 2013;17(19):2578-86.

Kim et al., The current status of bladder preservation in the treatment of muscle invasive bladder cancer. J Urol. Sep. 2000;164(3 Pt 1):627-32. doi: 10.1097/00005392-200009010-00002.

Kiss et al., Kinetic analysis of the toxicity of pharmaceutical excipients Cremophor EL and RH40 on endothelial and epithelial cells. J Pharm Sci. Apr. 2013;102(4):1173-81. doi: 10.1002/jps.23458. Epub Jan. 29, 2013.

Meydani et al., Dietary polyphenols and obesity. Nutrients. Jul. 2010;2(7):737-51. doi: 10.3390/nu2070737. Epub Jul. 8, 2010.

Meydani, Curcumin modulation of angiogenesis and obesity. J Clin Biochem. Sep. 2011;44(13):S238-9. doi: 10.1016/.clinbiochem.2011.08.583.

Naksuriya et al., Curcumin nanoformulations: a review of pharmaceutical properties and preclinical studies and clinical data related to cancer treatment. Biomaterials. Mar. 2014;35(10):3365-83. doi: 10.1016/j.biomaterials.2013.12.090. Epub Jan. 15, 2014.

Perez-Torres et al., Hibiscus sabdariffa Linnaeus (Malvaceae), curcumin and resveratrol as alternative medicinal agents against metabolic syndrome. Cardiovasc Hematol Agents Med Chem. Mar. 2013;11(1):25-37. doi: 10.2174/1871525711311010006.

Rachmawati et al., Size-Dependent of Oil Droplet of Curcumin Nanoemulsion on the In Vivo Release Kinetic of Curcumin After Oral and Intravenous Administrations in Animal Model. Adv Sci Eng Med. Sep. 2014;6(9):959-64.

Rayalam et al., Resveratrol induces apoptosis and inhibits adipogenesis in 3T3-L1 adipocytes. Phytother Res. Oct. 2008;22(10):1367-71. doi: 10.1002/ptr.2503.

Shafaghi et al., Prevalence of overweight and obesity among secondary school children (12-14 yr) in the city of Mashhad, Iran, Nov. 2010. Clin Biochem. Sep. 2011;44(13):S238-9. doi: 10.1016/j.clinbiochem.2011.08.581.

Yan et al., The study of weight control and the mechanism on the model of simplicity obesity rats by curcumin. J Xi'an Jiaotong Univ (Medical Sciences). Aug. 2006;27(4):387-90.

Zheng et al., Effects of puerarin on lipid accumulation and metabolism in high-fat diet-fed mice. PLoS One. Mar. 30, 2015;10(3):e0122925(1-11). doi: 10.1371/journal.pone.0122925.

PHARMACEUTICAL COMPOSITION FOR REDUCING LOCAL FAT AND USES THEREOF

RELATED APPLICATION

This application is a continuation-in-part application of U.S. patent application Ser. No. 15/754,429, filed Feb. 22, 2018, now U.S. Pat. No. 10,610,496, which is a U.S. national stage application of International Application No. PCT/IB2016/055102, filed Aug. 26, 2016, which claims the benefit of the filing dates of U.S. Provisional Application No. 62/299,702, filed Feb. 25, 2016 and U.S. Provisional Application No. 62/257,846, filed Nov. 20, 2015. The entire contents of each prior application is incorporated by reference herein.

FIELD OF THE INVENTION

The present invention relates to a pharmaceutical composition for reducing localized fat, specifically, relates to a pharmaceutical composition comprising drug-containing micelles and curcumin encapsulated in the micelles, and the pharmaceutical composition is for localized fat reduction.

BACKGROUND OF THE INVENTION

In recent years, more and more people have changed their views of beauty and raised their standards of individual health and body shape. As a result, people are not only concerned about weight loss, but focus more on reducing localized fat or contouring body shape in order to be healthier and achieve better body shape. Furthermore, common weight loss regimens, whether it is through diet or exercise, cannot reduce fat at a specific location. Currently, if wanting to reduce localized fat at specific locations (such as the waist, abdomen, legs, arms, chin, and face, etc), the only available technology is liposuction.

At present, liposuction is the most prevalent technology to reduce localized fat. However, the procedure of liposuction causes severe damages to the nerves, blood vessels, and other tissues. Liposuction also comes with risks of infections, severe bleeding, prolonged anesthesia, and unpredictable life-threatening conditions such as fat embolism and allergic reactions to anesthesia. In addition, it is common to experience significant bruising and swelling, severe pain, and post-operational recovery can take as long as 3 to 6 months, and the liposuction site may become uneven. Therefore, statistical analyses revealed that even though many people have considered liposuction to reduce the accumulation of localized subcutaneous fat or improve body curves, less than 40 percent of them actually went through liposuction. It shows that the customers who want to improve body curves or reduce localized fat are deterred from the problems of side effects of liposuction, pain after liposuction, or risks of liposuction.

Although some non-surgical localized fat-reducing pharmaceutical compositions or equipments can partially lower the side effects, they are usually not effective and come with other side effects, such as necrosis of surrounding normal cells, inflammation of surrounding tissues, and sharp pain. Additionally, their administration sites are limited. Therefore, the market is eagerly demanding for an effective localized fat-reducing pharmaceutical composition that has less side effects, a better safety profile, and a shorter recovery period.

In case of the customers and doctors have significant high demand, the pressing concern is to develop a localized fat-reducing pharmaceutical composition that breaks through the limits of current technologies.

SUMMARY OF THE INVENTION

In view of the deficiency of prior arts, the present invention provides a pharmaceutical composition for reducing localized fat, comprising drug-containing micelles made of surfactants, and curcumin encapsulated in said drug-containing micelles. The pharmaceutical composition for reducing localized fat can reduce the fat at the administration site, and has the advantages of high stability, high fat tissue bioavailability, few side effects, and sustained release.

The present invention can promote apoptosis of the local adipocytes at the administration sites, thereby achieving the goal of reducing localized fat. The present invention drastically improves the adverse reactions and side effects of the prior arts such as necrosis of the surrounding cells and inflammation reactions. The present invention is suitable for direct injection, subcutaneous implantation, intravenous injection, implanted infusion, cream, patch, and other skin absorption systemic delivery methods to administer at the sites requiring fat reduction without the need or assistance of any surgery or equipment. Preferably, it is administered locally at the subcutaneous fat layer via subcutaneous injection. Preferably, the injection formulation of the present pharmaceutical composition includes but is not limited to powder for injection, or powder for solution for injection. The localized fat mentioned herein includes but is not limited to the fat at the waist, the legs, the arms, the chin, and the face.

In the present invention, the term "turmeric extract" refers to the curcumin ingredient mixture extracted by any solvent and any extraction method, commercially available turmeric extract, any mixture containing at least 75% (wt %) of curcumin, any mixture containing at least 75% (wt %) of curcuminoid, or commercially available curcumin.

Wherein, curcuminoid is a collective term for curcumin, demethoxycurcumin, and bisdemethoxycurcumin.

In the present invention, the term "resveratrol" refers to the resveratrol extracted from natural plants or commercially available resveratrol. Preferably, the purity of resveratrol is 90% to 100% (wt %).

In the present invention, the term "green tea extract" refers to the green tea ingredient mixture extracted by any solvent and any extraction method, commercially available green tea extract, any mixture containing at least 45% of epigallocatechin gallate (EGCG), or commercially available epigallocatechin gallate (EGCG).

In the present invention, the term "micelle" refers to a microstructure formed by surfactants, wherein each of the surfactants has a hydrophilic end and a hydrophobic (lipophilic) end, and the surfactants are arranged in a way that the hydrophilic ends face outward and the hydrophobic (lipophilic) ends face inward to form the microstructure. Preferably, the microstructure is a spherical structure, a spheroidal structure, or other microstructural structures.

In the present invention, the term "drug-containing micelles" refer to the micelles containing curcuminoid. Preferably, drug-containing micelles refer to the micelles containing curcumin; that is, drug-containing micelles refer to the micelles encapsulating or containing curcuminoid. Preferably, drug-containing micelles refer to the micelles encapsulating or containing curcumin.

In the present invention, the term "second lipophilic drug-containing micelles" refer to the micelles containing any lipophilic drug except curcuminoid. That is, the second lipophilic drug-containing micelles refer to the micelles encapsulating or containing the second lipophilic drug.

Wherein, the term "other lipophilic drug (or the second lipophilic drug)" refers to at least one of quercetin, synephrine, puerarin, resveratrol, and any lipophilic drug except curcuminoid, or combination thereof. Or, the other lipophilic drug refers to any lipophilic drug except curcumin.

In the present invention, the term "hydrophilic drug" refers to at least one of green tea extract, epigallocatechin gallate, epicatechin, epicatechin gallate, epigallocatechin, gallocatechin gallate, gallocatechin, catechin gallate, catechin, epigallocatechin gallate (EGCG), caffeine, carnitine, L-carnitine, synephrine, chlorogenic acid, and other hydrophilic drugs, or combination thereof.

In the present invention, the term "state without precipitation", as used herein, refers to a state wherein no precipitation can be observed with the naked eye, that is, without the need by the assistance of artificial instruments.

In the present invention, the term "localized subcutaneous fat" refers to the subcutaneous fat at the site administered with the pharmaceutical composition, subcutaneous injection formulation, or subcutaneous fat layer injection formulation of the present invention.

In the present invention, the term "pharmaceutically acceptable solution" is at least one of water for injection, aqueous solution for injection, and normal saline, or combination thereof.

In the present invention, the term "local anesthetic" is at least one of amides, para-aminobenzoic acid esters, amino ethers, and other local anesthetic, or combination thereof. Preferably, the amides are at least one of dibucaine, lidocaine, mepivacaine HCl, bupivacine HCl, pyrrocaine HCl, prilocaine HCl, digammacaine, and oxethazaine, or combination thereof. Preferably, the para-aminobenzoic acid esters are at least one of butacaine, dimethocaine, and tutocaine, or combination thereof. Preferably, the amino ethers are at least one of quinisocaine and pramocaine, or combination thereof.

In the present invention, the term "antioxidant" is at least one of beta-carotene, lutein, lycopene, bilirubin, vitamin A, vitamin C (ascorbic acid), vitamin E, uric acid, nitric oxide, nitroxide, pyruvate, catalase, superoxide dismutase, glutathione peroxidases, N-acetyl cysteine, naringenin, and other antioxidant, or combination thereof.

In the present invention, the pharmaceutical composition maintains at a state without precipitation for at least 24 hours when it is subjected to accelerated stability test at 25° C.±2° C., relative humidity 60%±5%, and in the absence of direct light.

Or, the pharmaceutical composition maintains at a state without precipitation for at least 6 months when it is subjected to accelerated stability test at 25° C.±2° C., relative humidity 60%±5%, and in the absence of direct light.

The present invention provides a pharmaceutical composition to be administered at a local site of a subject, comprising:
  drug-containing micelles; and
  curcuminoid encapsulated in said drug-containing micelles;
wherein, said drug-containing micelles are a microstructure formed by a pharmaceutically acceptable polyoxyethylene castor oil derivative, and the hydrophilic-lipophilic balance value (HLB value) of the polyoxyethylene castor oil derivative is greater than 10.

The present invention provides a pharmaceutical composition to be administered at a local site of a subject, comprising:
  drug-containing micelles; and
  curcuminoid encapsulated in said drug-containing micelles;
wherein, said drug-containing micelles are a microstructure formed by a pharmaceutically acceptable polyoxyethylene, and the hydrophilic-lipophilic balance value (HLB value) of the polyoxyethylene is greater than 10.

Preferably, the pharmaceutical composition further comprises a pharmaceutically acceptable aqueous solution, and said drug-containing micelles are evenly distributed in said pharmaceutically acceptable aqueous solution.

Preferably, the polyoxyethylene castor oil derivative is at least one of KOLLIPHOR® ELP (also known as CREMOPHOR® ELP, polyoxyl 35 castor oil), CREMOPHOR® RH 40 (polyoxyl 40 hydrogenated castor oil), and other polyoxyethylene castor oil derivatives, or combination thereof.

Preferably, the polyoxyethylene is at least one of polyoxyl 35 hydrogenated castor oil, polyoxyl 40 hydrogenated castor oil, polyoxyl 15 hydroxystearate, and other polyoxyethylenes, or combination thereof.

Preferably, the weight ratio of the curcuminoid to the polyoxyethylene is 1:5~1:500.

Preferably, the weight ratio of the curcuminoid to the polyoxyethylene is 1:8~1:500.

Preferably, the weight ratio of the curcuminoid to the polyoxyethylene is 1:20~1:150.

Preferably, the weight ratio of the curcuminoid to the polyoxyethylene castor oil derivative is 1:8~1:500.

Preferably, the weight ratio of the curcuminoid to the polyoxyethylene castor oil derivative is 1:20~1:150.

Preferably, the concentration of curcuminoid in the pharmaceutical composition is 0.3-120 mg/g.

Preferably, the concentration of curcuminoid in the pharmaceutical composition is 2-91 mg/g.

Preferably, the diameter of the drug-containing micelles is 3~50 nm.

Preferably, the diameter of the drug-containing micelles is 5~20 nm.

Preferably, the curcuminoid is curcumin.

Preferably, the pharmaceutical composition further comprises second lipophilic drug-containing micelles, and the second lipophilic drug-containing micelles are evenly distributed in the pharmaceutically acceptable aqueous solution; the second lipophilic-drug containing micelle is a second microstructure formed by a second polyoxyethylene castor oil derivative, and a second lipophilic drug is encapsulated in said second drug-containing micelles.

Preferably, the hydrophilic-lipophilic balance value (HLB value) of the second polyoxyethylene castor oil derivative is greater than 10.

Preferably, the pharmaceutical composition further comprises second lipophilic drug-containing micelles, and the second lipophilic drug-containing micelles are evenly distributed in the pharmaceutically acceptable aqueous solution; the second lipophilic-drug containing micelle is a second microstructure formed by a second polyoxyethylene, and a second lipophilic drug is encapsulated in said second drug-containing micelles.

Preferably, the hydrophilic-lipophilic balance value (HLB value) of the second polyoxyethylene is greater than 10.

Preferably, the second polyoxyethylene castor oil derivative is at least one of KOLLIPHOR® ELP (also known as CREMOPHOR® ELP; polyoxyl 35 castor oil), CREMO- PHOR® RH 40 (polyoxyl 40 hydrogenated castor oil), and other polyoxyethylene castor oil derivatives, or combination thereof.

Preferably, the second polyoxyethylene is at least one of polyoxyl 35 hydrogenated castor oil, polyoxyl 40 hydrogenated castor oil, polysorbate 80 (TWEEN® 80), polyoxyl 15 hydroxystearate, and other polyoxyethylenes, or combination thereof.

Preferably, the second lipophilic drug is at least one of quercetin, synephrine, puerarin, resveratrol, and any other lipophilic drug except curcuminoid, or combination thereof.

Preferably, the weight ratio of the curcuminoid to the second lipophilic drug is 30:1~1:10.

Preferably, the weight ratio of the curcuminoid to the second lipophilic drug 20:1~1:8.

Preferably, the pharmaceutically acceptable aqueous solution further comprises a hydrophilic drug.

Preferably, the hydrophilic drug is at least one of green tea extract, epigallocatechin gallate, epicatechin, epicatechin gallate, epigallocatechin, gallocatechin gallate, gallocatechin, catechin gallate, catechin, epigallocatechin gallate (EGCG), caffeine, carnitine, L-carnitine, synephrine, chlorogenic acid, and other hydrophilic drugs, or combination thereof.

Preferably, the weight ratio of the curcuminoid to the hydrophilic drug is 30:1 to 1:10.

Preferably, the concentration of epigallocatechin gallate (EGCG) in the pharmaceutical composition is 0.1~15 mg/mL.

Preferably, the pharmaceutical composition further comprises a cosolvent to increase the solubility of drugs.

Preferably, the cosolvent is at least one of polyethylene glycol, propylene glycol, ethanol, and other cosolvents, or combination thereof.

Preferably, the polyethylene glycol is at least one of PEG 200, PEG 400, PEG 600, and other polyethylene glycols, or combination thereof.

Preferably, the pharmaceutical composition further comprises a suspending agent to reduce the sedimentation rate of drugs or micelles.

Preferably, the suspending agent is at least one of sodium alginate, glycerol, carboxymethylcellulose sodium, mannitol, and other suspending agents, or combination thereof.

Preferably, the pharmaceutical composition further comprises an oil phase excipient to increase the stability of the pharmaceutical composition and the solubility of drugs.

Preferably, the oil phase excipient is at least one of unsaturated fatty acids, glycerol, triglycerides, and other oil phase excipients, or combination thereof.

Preferably, the unsaturated fatty acids are at least one of oleic acid, castor oil, sesame oil, cottonseed oil, soybean oil, safflower oil, corn oil, and other unsaturated fatty acids, or combination thereof.

Preferably, the triglycerides are at least one of medium chain triglycerides, and other triglycerides, or combination thereof.

Preferably, the pharmaceutical acceptable aqueous solution comprises a local anesthetic.

Preferably, the pharmaceutically acceptable aqueous solution comprises an antioxidant.

The present invention further provides a use of the pharmaceutical composition in preparing a subcutaneous injection formulation, a subcutaneous fat layer injection formulation, a subcutaneous implanted device, a subcutaneous implant, an intravenous injection formulation, a solution for implanted infusion, a cream, a patch, or other skin-absorption delivery systems.

Preferably, the pharmaceutical composition further comprises second lipophilic drug-containing micelles, and the second lipophilic drug-containing micelles are evenly distributed in the pharmaceutically acceptable aqueous solution; wherein, the second lipophilic drug-containing micelle is a second microstructure formed by a second non-ionic surfactant, and a second lipophilic drug is encapsulated in said second lipophilic drug-containing micelles.

Preferably, the second non-ionic surfactant is at least one of polysorbate 80 (TWEEN® 80), polyoxyl 15 hydroxystearate (SOLUTOL® HS 15), polyoxyethylene castor oil derivatives, and other non-ionic surfactants, or combination thereof.

Preferably, the polyoxyethylene castor oil derivative is at least one of KOLLIPHOR® ELP (also known as CREMOPHOR® ELP, polyoxyl 35 castor oil), CREMOPHOR® RH 40 (polyoxyl 40 hydrogenated castor oil), and other polyoxyethylene castor oil derivatives, or combination thereof.

Preferably, the pharmaceutically acceptable aqueous solution further comprises a hydrophilic drug.

The present invention further provides a use of the pharmaceutical composition in preparing a drug or a subcutaneous injection formulation for reducing localized subcutaneous fat; the pharmaceutical composition comprises:
  drug-containing micelles; and
  curcuminoid encapsulated in said drug-containing micelles;
wherein, the drug-containing micelle is a microstructure formed by a pharmaceutically acceptable non-ionic surfactant, and the hydrophilic-lipophilic balance value (HLB value) of the non-ionic surfactant is greater than 10.

Preferably, the pharmaceutical composition further comprises a pharmaceutically acceptable aqueous solution, and said drug-containing micelles are evenly distributed in said pharmaceutically acceptable aqueous solution.

Preferably, the non-ionic surfactant is at least one of polysorbate 80 (TWEEN® 80), polyoxyl 15 hydroxystearate (SOLUTOL® HS 15), polyoxyethylene castor oil derivatives, and other non-ionic surfactants, or combination thereof.

Preferably, the polyoxyethylene castor oil derivative is at least one of KOLLIPHOR® ELP (also known as CREMOPHOR® ELP, polyoxyl 35 castor oil), CREMOPHOR® RH 40 (polyoxyl 40 hydrogenated castor oil), and other polyoxyethylene castor oil derivatives, or combination thereof.

Preferably, the weight ratio of the curcuminoid to the non-ionic surfactant is 1:8 to 1:500.

Preferably, the concentration of curcuminoid in the pharmaceutical composition is 0.3~120 mg/g.

Preferably, the diameter of the drug-containing micelles is 3~50 nm.

Preferably, the pharmaceutical composition further comprises second lipophilic drug-containing micelles, and the second lipophilic drug-containing micelles are evenly distributed in the pharmaceutically acceptable aqueous solution; wherein, the second lipophilic drug-containing micelle is a second microstructure formed by a second non-ionic surfactant, and a second lipophilic drug is encapsulated in said second lipophilic drug-containing micelles.

Preferably, the hydrophilic-lipophilic balance value (HLB value) of the second non-ionic surfactant is greater than 10.

Preferably, the second non-ionic surfactant is at least one of polysorbate 80 (TWEEN® 80), polyoxyl 15 hydroxystearate (SOLUTOL® HS 15), polyoxyethylene castor oil derivatives, and other non-ionic surfactants, or combination thereof.

Preferably, the second non-ionic surfactant is at least one of KOLLIPHOR® ELP (also known as CREMOPHOR® ELP, polyoxyl 35 castor oil), CREMOPHOR® RH 40 (polyoxyl 40 hydrogenated castor oil), and other polyoxyethylene castor oil derivatives, or combination thereof.

Preferably, the second lipophilic drug is at least one of quercetin, synephrine, puerarin, resveratrol, and any other lipophilic drug except curcuminoid, or combination thereof.

Preferably, the weight ratio of the curcuminoid to the second lipophilic drug is 30:1~1:10.

Preferably, the weight ratio of the curcuminoid to the lipophilic drug 20:1~1:8.

Preferably, the pharmaceutically acceptable aqueous solution further comprises a hydrophilic drug.

Preferably, the hydrophilic drug is at least one of green tea extract, epigallocatechin gallate, epicatechin, epicatechin gallate, epigallocatechin, gallocatechin gallate, gallocatechin, catechin gallate, catechin, epigallocatechin gallate (EGCG), caffeine, carnitine, L-carnitine, synephrine, chlorogenic acid, and other hydrophilic drugs, or combination thereof.

Preferably, the weight ratio of the curcuminoid to the hydrophilic drug is 30:1 to 1:10.

Preferably, the weight ratio of the curcuminoid to the hydrophilic drug is 20:1 to 1:8.

Preferably, the formulation of the drug is subcutaneous injection formulation, subcutaneous fat layer injection formulation, solution for implanted infusion, cream formulation, patch formulation, or other skin-absorption delivery systems.

Preferably, the drug is to be administered at an administration site to reduce the subcutaneous fat at the administration site.

Preferably, the formulation of the drug is subcutaneous injection formulation or subcutaneous fat layer injection formulation, and the administered dosage of the drug to be injected at the local site is 0.02~20 mg/cm$^2$.

The formulation of the drug is subcutaneous injection formulation or subcutaneous fat layer injection formulation, and the administered dosage of the drug to be injected is 0.04~16 mg/cm$^2$ Preferably, the formulation of the drug is subcutaneous injection formulation or subcutaneous fat layer injection formulation, and the administered dosage of the drug to be injected is 0.01~40 mg/kg.

Preferably, the formulation of the drug is subcutaneous injection formulation or subcutaneous fat layer injection formulation, and the administered dosage of the drug to be injected is 0.1~20 mg/kg.

Preferably, the dosing frequency of the drug to be administered at the administration site is 1~12 times every other day to every 30 days.

Preferably, the dosing frequency of the drug to be administered at the administration site is 1~6 times every other day to every 30 days.

Preferably, the curcuminoid is curcumin.

Preferably, the pharmaceutical composition further comprises at least one of a cosolvent, a suspending agent, and an oil phase excipient, or combination thereof.

Preferably, the microstructure is co-formed by the non-ionic surfactant and at least one of the oil phase excipient and cosolvent.

The present invention further provides a use of a pharmaceutical composition in preparing a drug or a subcutaneous injection formulation for reducing weight; the pharmaceutical composition comprises:

drug-containing micelles; and
curcuminoid encapsulated in said drug-containing micelles;
wherein, the drug-containing micelle is a microstructure formed by a pharmaceutically acceptable non-ionic surfactant, and the hydrophilic-lipophilic balance value (HLB value) of the non-ionic surfactant is greater than 10.

Preferably, the pharmaceutical composition further comprises a pharmaceutically acceptable aqueous solution, and said drug-containing micelles are evenly distributed in said pharmaceutically acceptable aqueous solution.

Preferably, the curcuminoid is curcumin.

Preferably, the pharmaceutical composition further comprises second lipophilic drug-containing micelles, and the second lipophilic drug-containing micelles are evenly distributed in the pharmaceutically acceptable aqueous solution; wherein, the second lipophilic drug-containing micelle is a second microstructure formed by a second non-ionic surfactant, a second lipophilic drug is encapsulated in said second lipophilic drug-containing micelles, and the second lipophilic drug is at least one of quercetin, synephrine, puerarin, resveratrol, and any other lipophilic drug except curcuminoid, or combination thereof.

Preferably, the pharmaceutically acceptable aqueous solution further comprises a hydrophilic drug, and the hydrophilic drug is at least one of green tea extract, epigallocatechin gallate, epicatechin, epicatechin gallate, epigallocatechin, gallocatechin gallate, gallocatechin, catechin gallate, catechin, epigallocatechin gallate (EGCG), caffeine, carnitine, L-carnitine, synephrine, chlorogenic acid, and other hydrophilic drugs, or combination thereof.

Preferably, the formulation of the drug is subcutaneous injection formulation, intravenous injection formulation, or subcutaneous fat layer injection formulation, and the administered dosage of the drug to be injected is 0.2~16 mg/cm$^2$.

Preferably, the formulation of the drug is subcutaneous injection formulation, intravenous injection formulation, or subcutaneous fat layer injection formulation, and the administered dosage of the drug to be injected is 0.4~8 mg/cm$^2$.

Preferably, the formulation of the drug is subcutaneous injection formulation, intravenous injection formulation, or subcutaneous fat layer injection formulation, and the administered dosage of the drug to be administered is 0.4~40 mg/kg.

Preferably, the formulation of the drug is subcutaneous injection formulation, intravenous injection formulation, or subcutaneous fat layer injection formulation, and the administered dosage of the drug to be injected is 0.8~20 mg/kg.

Preferably, the dosing frequency of the drug to be administered at the administered site is 3~60 times every other day to every 20 days.

Preferably, the dosing frequency of the drug to be administered at the administered site is 6~42 times every other day to every 14 days.

Preferably, the pharmaceutical composition further comprises at least one of a cosolvent, a suspending agent, and an oil phase excipient, or combination thereof.

Preferably, the microstructure is co-formed by the non-ionic surfactant and at least one of the oil phase excipient and cosolvent.

The present invention provides a method for reducing subcutaneous fat at a local site of a subject, comprising a step of administering a pharmaceutical composition at the local site of the subject, wherein, the pharmaceutical composition comprises:

drug-containing micelles; and
curcuminoid encapsulated in said drug-containing micelles;

wherein, the drug-containing micelle is a microstructure formed by a pharmaceutically acceptable non-ionic surfactant, and the hydrophilic-lipophilic balance value (HLB value) of the non-ionic surfactant is greater than 10.

Preferably, the step is to administer the pharmaceutical composition at the local site of the subject with a subcutaneous injection formulation, a subcutaneous fat layer injection formulation, a solution for implanted infusion, cream formulation, a patch formulation, or other skin-absorption delivery systems.

Preferably, the administered dosage of the pharmaceutical composition to be injected at the local site of the subject is 0.02~20 mg/cm$^2$.

Preferably, the administered dosage of the pharmaceutical composition to be injected at the local site of the subject is 0.01~40 mg/kg.

Preferably, the dosing frequency of the pharmaceutical composition to be administered at the local site of the subject is 1~12 times every other day to every 30 days.

The present invention provides a method for reducing body weight of a subject, comprising a step of administering a pharmaceutical composition to the subject, wherein, the pharmaceutical composition comprises:
  drug-containing micelles; and
  curcuminoid encapsulated in said drug-containing micelles;
wherein, the drug-containing micelle is a microstructure formed by a pharmaceutically acceptable non-ionic surfactant, and the hydrophilic-lipophilic balance value (HLB value) of the non-ionic surfactant is greater than 10.

Preferably, the step is to administer the pharmaceutical composition at the local site of the subject with a subcutaneous injection formulation, an intravenous injection formulation, or a subcutaneous fat layer injection formulation.

Preferably, the administered dosage of the pharmaceutical composition to be injected at the local site of the subject is 0.2~16 mg/cm$^2$.

Preferably, the administered dosage of the pharmaceutical composition to be injected at the local site of the subject is 0.4~40 mg/kg.

Preferably, the dosing frequency of the pharmaceutical composition to be administered at the local site of the subject is 3~60 times every other day to every 20 days.

Preferably, the step is to administer the pharmaceutical composition at the local site of the subject with a subcutaneous injection formulation, a subcutaneous fat layer injection formulation, an intravenous injection formulation, a solution for implanted infusion, a cream, a patch, or other skin-absorption delivery systems.

DETAILED DESCRIPTION OF THE INVENTION

Experiment 1: The Effects of Orally Administered Turmeric Extract on the Amount of the Subcutaneous Fat and the Body Weight of Rats.

The turmeric extract oral liquid was prepared as follows: An appropriate amount of sterile water for injection was added to an appropriate amount of turmeric extract and mixed well to obtain the turmeric extract oral liquid.

Seven-week-old male Sprague-Dawley rats were used for the experiment. First, 12 rats were fed with high-fat diet (Research Diets, Inc.; Cat #D12492) to induce the accumulation of subcutaneous fat until each rat weighed 330±10 g, and the rats were randomly assigned into two groups, which were a high-fat diet control group, a turmeric extract oral administration group, with 6 rats in each group such that there was no statistical difference in the body weight between groups. The body weight of each rat was recorded and defined as the "pre-experimental body weight" of each rat. Then, drugs were administered as follows:

Turmeric extract oral administration group: the rats were fed with high-fat diet daily and administered with turmeric extract oral liquid via oral gavage, and the administered dosage of turmeric extract was 100 mg/kg/day, and the rats were fed for 20 consecutive days. The concentration of curcumin in the turmeric extract oral liquid is 95% (wt %).

High-fat diet control: rats were fed with high-fat diet daily but were not fed with turmeric extract.

Changes of the body weight were recorded daily during the period of the experiment, and water and food consumption was recorded weekly. The rats were fasted on day 20 and euthanized on day 21.

The body weight of each rat was recorded and defined as the "post-experimental body weight" of each rat. The "total body weight gain" of each rat was obtained by subtracting its "pre-experimental body weight" from its "post-experimental body weight". Finally, the bilateral lower inguinal subcutaneous fat pads were dissected and weighed, and the amount of the inguinal fat of each group was calculated. The data were presented as mean±SD and statistically analyzed. The statistical results were shown as symbols or letters, wherein different symbols or letters indicates statistically significant difference ($p<0.05$), and identical symbols or letters indicates no statistical significance ($p>0.05$).

Figure 1A:
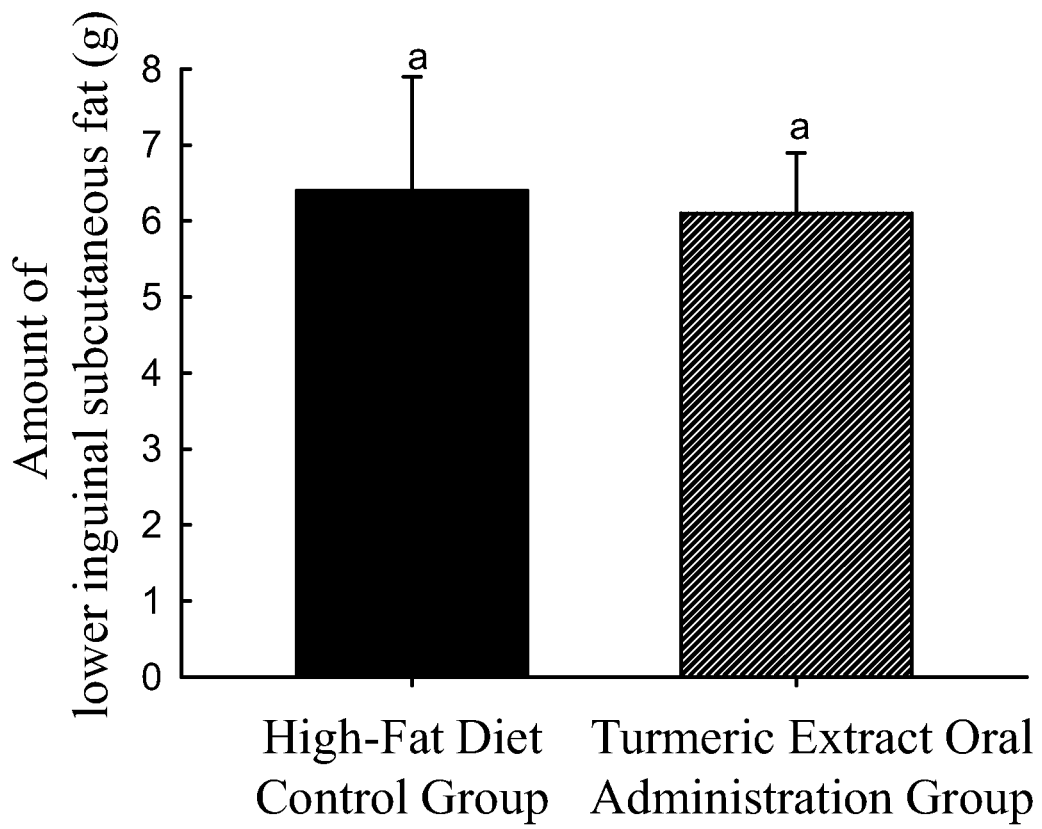
FIG. 1A: A bar graph showing the effects of turmeric extract on the amount of subcutaneous fat of rats by way of oral administration.
Figure 1B:
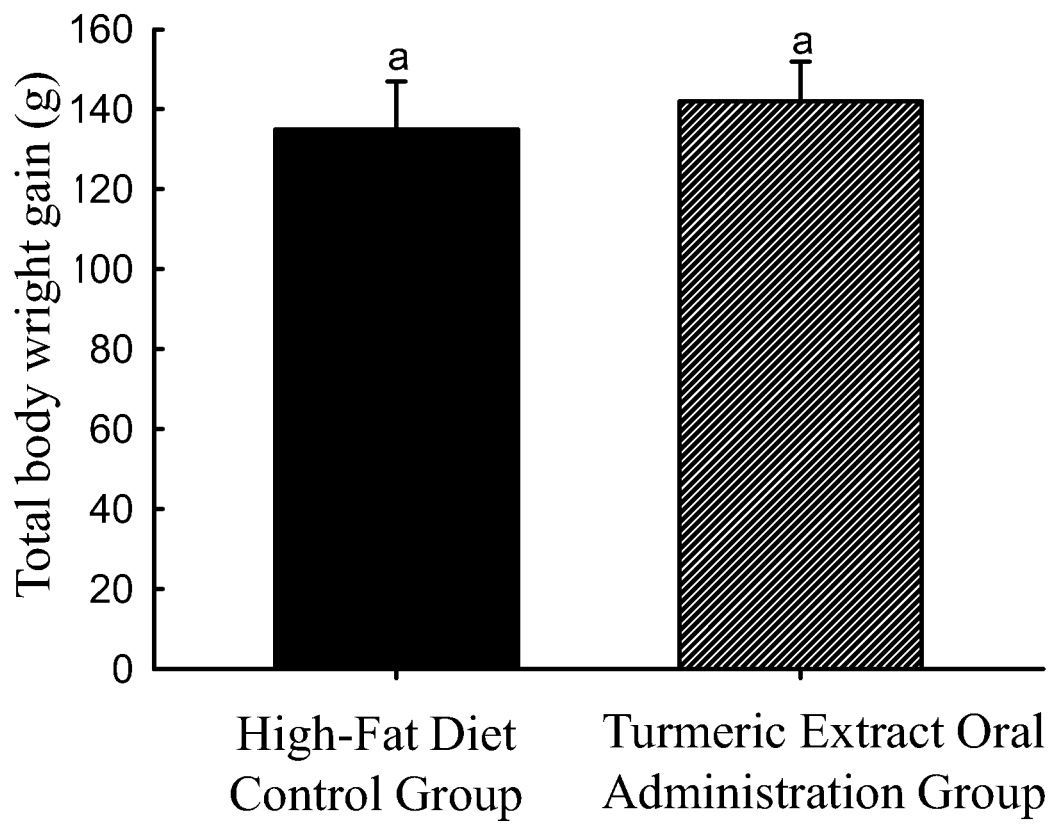
FIG. 1B: A bar graph showing the effects of turmeric extract on total body weight gain of rats by way of oral administration.

Please refer to FIG. 1A and FIG. 1B. FIG. 1A is a bar graph showing the effect of turmeric extract on the amount of subcutaneous fat of rats via oral administration. Wherein, said inguinal subcutaneous fat is the total amount of bilateral inguinal subcutaneous fat. FIG. 1B is a bar graph showing the effects of turmeric extract on total body weight gain of rats via oral administration.

As shown in FIG. 1A, the inguinal subcutaneous fat of the rats in high-fat diet control group is 6.4±1.5 g, and the inguinal subcutaneous fat of the rats in turmeric extract oral administration group is 6.1±0.8 g, and there is no statistical significance between groups ($p>0.05$). This demonstrated that oral administration of turmeric extract cannot reduce localized fat.

As shown in FIG. 1B, the total body weight gain of the rats in high-fat diet control group is 135±12 g, and the total body weight gain of the rats in high-fat diet control group is 142±10 g, and there was no statistical significance between groups ($p>0.05$). This demonstrated that oral administration of turmeric extract cannot reduce the body weight.

The above experiments demonstrated that orally administrated turmeric extract cannot reduce the localized fat nor can it reduce the body weight. In order to solve this problem, the inventor conducted further studies to develop the pharmaceutical composition comprising curcumin and the subcutaneous injection formulation thereof.

Experiment 2: The Effects of Curcumin Subcutaneous Injection Formulation on the the Amount of Subcutaneous Fat and the Body Weight of Rats.

A curcumin normal saline solution, a curcumin PEG solution, and a curcumin ELP solution were prepared as follows:

Preparation of the Curcumin Normal Saline Solution:

450 mg of curcumin was mixed with an appropriate amount of normal saline for injection to a total volume of 90 mL. The solution was mixed well to completely dissolve curcumin to obtain the curcumin normal saline solution, and the concentration of curcumin in said curcumin normal saline solution was 5 mg/mL.

Preparation of the Curcumin PEG Solution.

15 g of polyethylene glycol 400 (PEG 400) and 15 g of glycerol were mixed with an appropriate amount of normal saline for injection to a total volume of 100 mL. The solution was mixed well to completely dissolve PEG 400 and glycerol to obtain a PEG and glycerol mixture. 450 mg of curcumin was mixed with an appropriate amount of the PEG and glycerol mixture to a total volume of 90 mL. The solution was mixed well to completely dissolve curcumin to obtain the curcumin PEG solution. The concentration of curcumin in said curcumin PEG solution was 5 mg/mL.

Preparation of the Curcumin ELP Solution:

450 mg of curcumin was mixed with 80~140 mL of dichloromethane, and stirred at 150~500 rpm at room temperature until curcumin dissolved completely. 18 g of KOLLIPHOR® ELP (also known as CREMOPHOR® ELP (polyoxyl 35 castor oil, abbreviated as ELP) was added to the solution and stirred well at 100~300 rpm to volatilize dichloromethane. Once dichloromethane volatilized completely, normal saline for injection was slowly added to a total volume of 90 mL, and the solution was mixed well to obtain the curcumin ELP solution. In said curcumin ELP solution, the concentration of curcumin was 5 mg/mL, the ELP concentration was approximately 20% (wt %), and the weight ratio of curcumin to ELP was 1:40.

Six-week-old male Sprague-Dawley rats were used for the experiment. First, 20 rats were fed with high-fat diet (Research Diets, Inc.; Cat #D12492) to induce the accumulation of subcutaneous fat. Feeding was continued until each rat weighed 330±10 g, and the rats were randomly assigned into four groups, which were a control group, a normal saline group, a PEG group, and an ELP group, with 5 rats in each group such that there was no statistical difference in the body weight between groups. The body weight of each rat was recorded and defined as the "pre-experimental body weight" of each rat. Then, drugs were administered as follows:

The curcumin normal saline, the curcumin PEG solution, and the curcumin ELP solution were injected to the inguinal subcutaneous fat pads of rats in the normal saline group, the PEG group, and the ELP group, respectively. Each injection volume was 4 mL per kilogram of body weight (4 mL/kg), such that each injected dosage was 20 mg of curcumin per kilogram of body weight (20 mg/kg; 4 mL/kg×5 mg/mL=20 mg/kg). Rats in the control group were injected with the same volume of normal saline in the same manner described above.

The injection sites mentioned above were the lower inguinal fat pads of rats. Bilateral injections were administered evenly once a day on day 1, 2, 3, and 4 of the experiment. The rats were fed with high-fat diet for the entire duration of the experiment. Their weight changes were recorded daily, and food and water consumption was recorded weekly. The experiment lasted for 14 days, and the rats were euthanized by $CO_2$ on day 15.

The body weight of each rat was recorded and defined as the "post-experimental body weight" of each rat. The "total body weight gain" of each rat was obtained by subtracting its "pre-experimental body weight" from its "post-experimental body weight". The "relative weight gain" was obtained by dividing the total body weight gain of each group by the total body weight gain of the control group.

The bilateral lower inguinal subcutaneous fat pads of rats were dissected and weighed, and the weights of the bilateral lower inguinal subcutaneous fat pads were summed to calculate the amount of lower inguinal subcutaneous fat. The amount of lower inguinal subcutaneous fat of each group was divided by the amount of lower inguinal subcutaneous fat of the control group to obtain the "relative weight of the lower inguinal subcutaneous fat".

The data were presented as mean±SD and analyzed by one-way ANOVA. Statistical results were shown as symbols or letters. Different symbols or letters indicates statistically significant difference (p<0.05), and identical symbols or letters indicates no statistically significant difference (p>0.05).

Figure 2A:
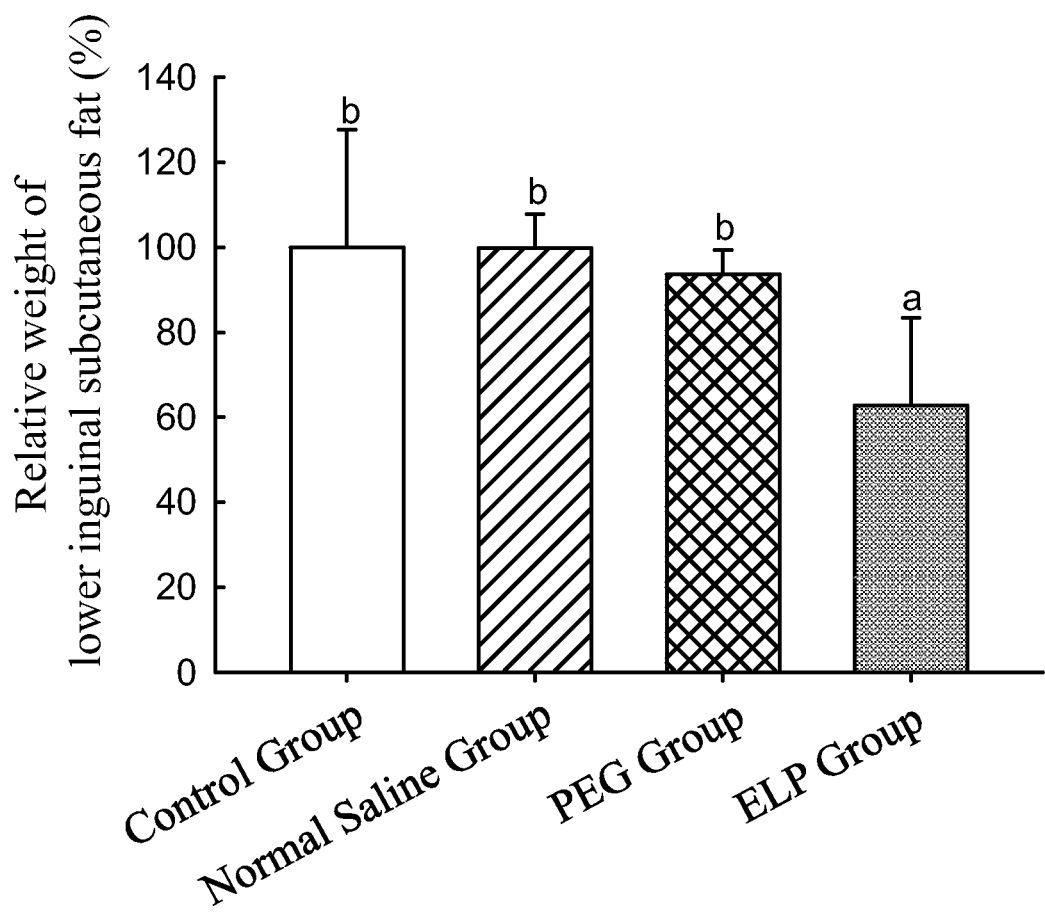
FIG. 2A: A bar graph showing the effects of curcumin subcutaneous injection formulations prepared with different excipients on the amount of localized subcutaneous fat of rats.
Figure 2B:
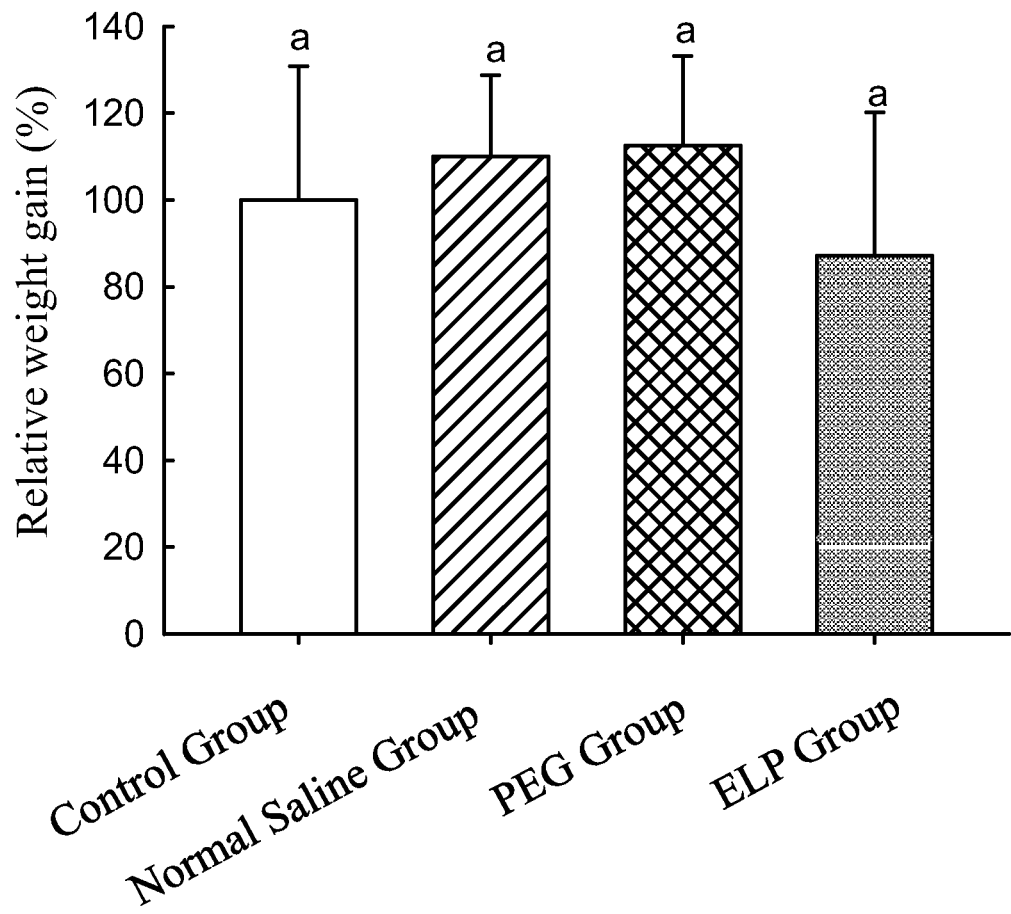
FIG. 2B: A bar graph showing the effects of curcumin subcutaneous injection formulations prepared with different excipients on total body weight gain of rats.

Please refer to FIG. 2A and FIG. 2B. FIG. 2A is a bar graph showing the effects of curcumin subcutaneous injection formulations prepared with different excipients on the amount of localized subcutaneous fat of rats. FIG. 2B is a bar graph showing the effects of curcumin subcutaneous injection formulations prepared with different excipients on total body weight gain of rats.

As shown in FIG. 2A, the relative weight of the lower inguinal subcutaneous fat of rats in the control group was 100±27.6%, the relative weight of the lower inguinal subcutaneous fat of rats in the normal saline group was 99.8±8.0%, the relative weight of the lower inguinal subcutaneous fat of rats in the PEG group was 93.6±5.8%, and the relative weight of the lower inguinal subcutaneous fat of rats in the ELP group was 62.8±20.5%. There was no significant difference in the relative weight of the lower inguinal subcutaneous fat between the normal saline and the control group, suggesting that direct injection of curcumin to the subcutaneous fat layer of the administration site cannot reduce the fat at the administration site (localized fat). There was no significant difference in the relative weight of the lower inguinal subcutaneous fat between the PEG group and the control group; the relative weight of the lower inguinal subcutaneous fat of the ELP group was significantly different (p<0.05) from that of the control group, and the relative weight of the lower inguinal subcutaneous fat of rats in the ELP group was reduced by 37.2%, As shown in FIG. 2B, the relative weight gain of rats in the control group was 100.0±30.8%, the relative weight gain of rats in the normal saline group was 110.0±18.7%, the relative weight gain of rats in the PEG group was 112.5±20.7%, and the relative weight gain of rats in the ELP group was 87.1±33.1%. There was no statistical significance between the four groups (p>0.05), but the body weight of rats in the ELP group was 12.9% less than the body weight of rats in the control group, indicating a trend of body weight loss in rats of the ELP group.

The experiments above demonstrated that direct injection of curcumin to the subcutaneous fat layer of the administration site cannot reduce the fat at the administration site (localized fat), nor can it reduce the body weight. Direct injection of the curcumin composition comprising the excipient PEG (a commonly used suspending agent) to the subcutaneous fat layer of administration site cannot reduce the fat at the administration site (localized fat), nor can reduce body weight; however, injection of the curcumin composition comprising the non-ionic surfactant ELP to the subcutaneous fat layer of the administration site not only can reduce the fat at the administration site (localized fat), but can also lead to a trend of body weight loss. Thus, it is necessary to further investigate whether the curcumin mixture has to comprise non-ionic surfactants to reduce the fat at the administration site (localized fat) and to reduce body weight.

Further analysis showed that there were no micelles in the administered curcumin PEG solution mentioned above, but there were micelles in the curcumin ELP solution, and curcumin was encapsulated in the micelles formed by ELP. Thus, it is necessary to further investigate the effect of micelles on reducing localized fat and reducing body weight.

Experiment 3: The Effects of Curcumin Simple Composition Subcutaneous Injection Formulation Comprising Non-Ionic Surfactants on the Amount of Subcutaneous Fat and the Body Weight of Rats A curcumin partial micellar formulation, a curcumin HS-15 partial micellar formulation, a curcumin ELP micellar formulation, and a curcumin HS-15 micellar formulation were prepared as follows:

Preparation of the curcumin ELP partial micellar formulation: 20 g of KOLLIPHOR® ELP (also known as CREMOPHOR® ELP (polyoxyl 35 castor oil, abbreviated as ELP) was mixed with an appropriate amount of normal saline for injection to a total weight of 100 g. The solution was mixed well to completely dissolve ELP to obtain a 20% ELP solution. 400 mg of curcumin was mixed with an appropriate amount of the 20% ELP solution to a total weight of 80 g. The solution was mixed well to completely dissolve curcumin to obtain the curcumin ELP partial micellar formulation. The concentration of curcumin in said curcumin ELP partial micellar formulation was approximately 5 mg/mL, the concentration of ELP was approximately 20%, and the weight ratio of curcumin to ELP was approximately 1:40.

Preparation of the curcumin HS-15 partial micellar formulation: 20 g of KOLLIPHOR® HS-15 (HS-15) was mixed with an appropriate amount of normal saline for injection to a total weight of 100 g. The solution was mixed well to completely dissolve HS-15 to obtain a 20% HS-15 solution. 400 mg of curcumin was mixed with an appropriate amount of the 20% HS-15 solution to a total weight of 80 g. The solution was mixed well to completely dissolve curcumin to obtain the curcumin HS-15 partial micellar formulation. The concentration of curcumin in said curcumin HS-15 partial micellar formulation was approximately 5 mg/mL, the concentration of ELP was approximately 20% (wt %), and the weight ratio of curcumin to HS-15 was approximately 1:40.

Preparation of the curcumin ELP micellar formulation: same as the preparation of the curcumin ELP solution in Experiment 2.

Preparation of the curcumin HS-15 micellar formulation: 500 mg of curcumin was mixed with 80~140 mL of dichloromethane and stirred at 150~500 rpm at room temperature until curcumin dissolved completely. 20 g of KOLLIPHOR® HS-15 (HS-15) was added and stirred at 100~300 rpm to volatilize dichloromethane. Once dichloromethane volatilized completely, normal saline for injection was slowly added to a total volume of 100 g. The solution was mixed well to form drug-containing micelles to obtain the curcumin HS-15 micellar formulation. The concentration of curcumin in said curcumin HS-15 micellar formulation was approximately 5 mg/mL, the concentration of HS-15 was approximately 20%, and the weight ratio of curcumin to HS-15 was approximately 1:40.

The curcumin ELP partial micellar formulation, the curcumin HS-15 partial micellar formulation, the curcumin ELP micellar formulation, and the curcumin HS-15 micellar formulation were analyzed by a particle size analyzer to determine if micelles were present, and the diameters of the micelles were measured.

The results showed that both the curcumin ELP partial micellar formulation and the curcumin HS-15 partial micellar formulation had drug precipitates (curcumin precipitates), and had a lower number of drug-containing micelles. On the contrary, the curcumin ELP micellar formulation and the curcumin HS-15 micellar formulation were clear without any stratification, and had a higher number of drug-containing micelles.

In addition, the particle diameters of the micelles in the curcumin ELP partial micellar formulation, the curcumin HS-15 partial micellar formulation, the curcumin ELP micellar formulation, and the curcumin HS-15 micellar formulation were 13.16±0.18 nm, 13.18±1.45 nm, 12.43±0.40 nm, and 11.46±0.41 nm, respectively, and the PDI values were 0.22±0.03, 0.18±0.05, 0.28±0.05, and 0.18±0.04, respectively.

The results indicated that although the curcumin ELP partial micellar formulation and the curcumin HS-15 partial micellar formulation both had drug precipitates (curcumin precipitates), their supernates still contained micelles (diameter<250 nm and PDI value<0.4). Therefore, the curcumin ELP partial micellar formulation, the curcumin HS-15 partial micellar formulation, the curcumin ELP micellar formulation, and the curcumin HS-15 micellar formulation are all pharmaceutical compositions of the present invention.

Six-week-old male Sprague-Dawley rats were used for the experiment. First, 20 rats were fed with high-fat diet (Research Diets, Inc.; Cat #D12492) to induce the accumulation of subcutaneous fat. Feeding was continued until each rat weighed 330±10 g, and the rats were randomly assigned into 5 groups, which were a control group, an ELP partial micellar group, an HS-15 partial micellar group, an ELP micellar group, and an HS-15 micellar group, with 4 rats in each group such that there was no statistical difference in the body weight between groups. The body weight of each rat was recorded and defined as the "pre-experimental body weight" of each rat. Then, drugs were administered as follows:

The curcumin ELP partial micellar formulation, the curcumin HS-15 partial micellar formulation, the curcumin ELP micellar formulation, and the curcumin HS-15 micellar formulation were each prepared and mixed well (to evenly suspend the precipitates in the partial micellar formulations), and were injected into the lower inguinal subcutaneous fat layer of rats in the ELP partial micellar group, the HS-15 partial micellar group, the ELP micellar group, and the HS-15 micellar group, respectively. Each injection volume was 4 mL per kilogram of body weight (4 mL/kg), such that each injected dosage was 20 mg of curcumin per kilogram of body weight (20 mg/kg; 4 mL/kg×5 mg/mL=20 mg/kg). Rats in the control group were injected with the same volume of normal saline in the same manner described above.

The injection sites mentioned above were the lower inguinal fat pads of rats. Bilateral injections were administered evenly once a day on day 1, 2, 3, 4, 5, and 6 of the experiment. The rats were fed with high-fat diet for the entire duration of the experiment. Their weight changes were recorded daily, and food and water consumption was recorded weekly. The experiment lasted for 14 days, and the rats were euthanized by $CO_2$ on day 15.

The body weight of each rat was recorded and defined as the "post-experimental body weight" of each rat. The "total body weight gain" of each rat was obtained by subtracting its "pre-experimental body weight" from its "post-experimental body weight". The "relative weight gain" was obtained by dividing the total body weight gain of each group by the total body weight gain of the control group.

The bilateral lower inguinal subcutaneous fat pads of rats were dissected and weighed, and the weights of the bilateral lower inguinal subcutaneous fat pads were summed to calculate the amount of lower inguinal subcutaneous fat. The amount of lower inguinal subcutaneous fat of each group was divided by the amount of lower inguinal subcutaneous fat of the control group to obtain the "relative weight of the lower inguinal subcutaneous fat".

The data were presented as mean±SD and analyzed by one-way ANOVA. Statistical results were shown as symbols or letters. Different symbols or letters indicates statistically significant difference ($p<0.05$), and identical symbols or letters indicates no statistically significant difference ($p>0.05$).

Based on the formulation preparation methods and the results of particle size analysis above, the concentration of ELP and the concentration of curcumin in the curcumin ELP partial micellar formulation were identical to those of the curcumin ELP micellar formulation, only the number of drug-containing micelles differed. Thus, comparing to the control group, if the curcumin ELP partial micellar formulation cannot significantly reduce the localized fat at the administration site, but the curcumin ELP micellar formulation can significantly reduce the localized fat at the administration site, this indicates that formation of drug-containing micelles is the critical factor for curcumin compositions to significantly reduce the localized fat at the administration site.

Similarly, the concentration of HS-15 and the concentration of curcumin in the curcumin HS-15 partial micellar formulation were identical to those of the curcumin HS-15 micellar formulation, only the number of drug-containing micelles differed. Thus, comparing to the control group, if the curcumin HS-15 partial micellar formulation cannot significantly reduce the localized fat at the administration site, but the curcumin HS-15 micellar formulation can significantly reduce the localized fat at the administration site, this indicates that formation of drug-containing micelles is the critical factor for curcumin compositions to significantly reduce the localized fat at the administration site.

On the other hand, the concentration of ELP and the concentration of curcumin in the curcumin ELP partial micellar formulation were identical to those of the curcumin ELP micellar formulation, only the number of drug-containing micelles differed. Thus, comparing to the control group, if the curcumin ELP partial micellar formulation cannot significantly reduce the body weight, but the curcumin ELP micellar formulation can significantly reduce the body weight, this indicates that formation of drug-containing micelles is the critical factor for curcumin compositions to significantly reduce body weight.

Figure 3:
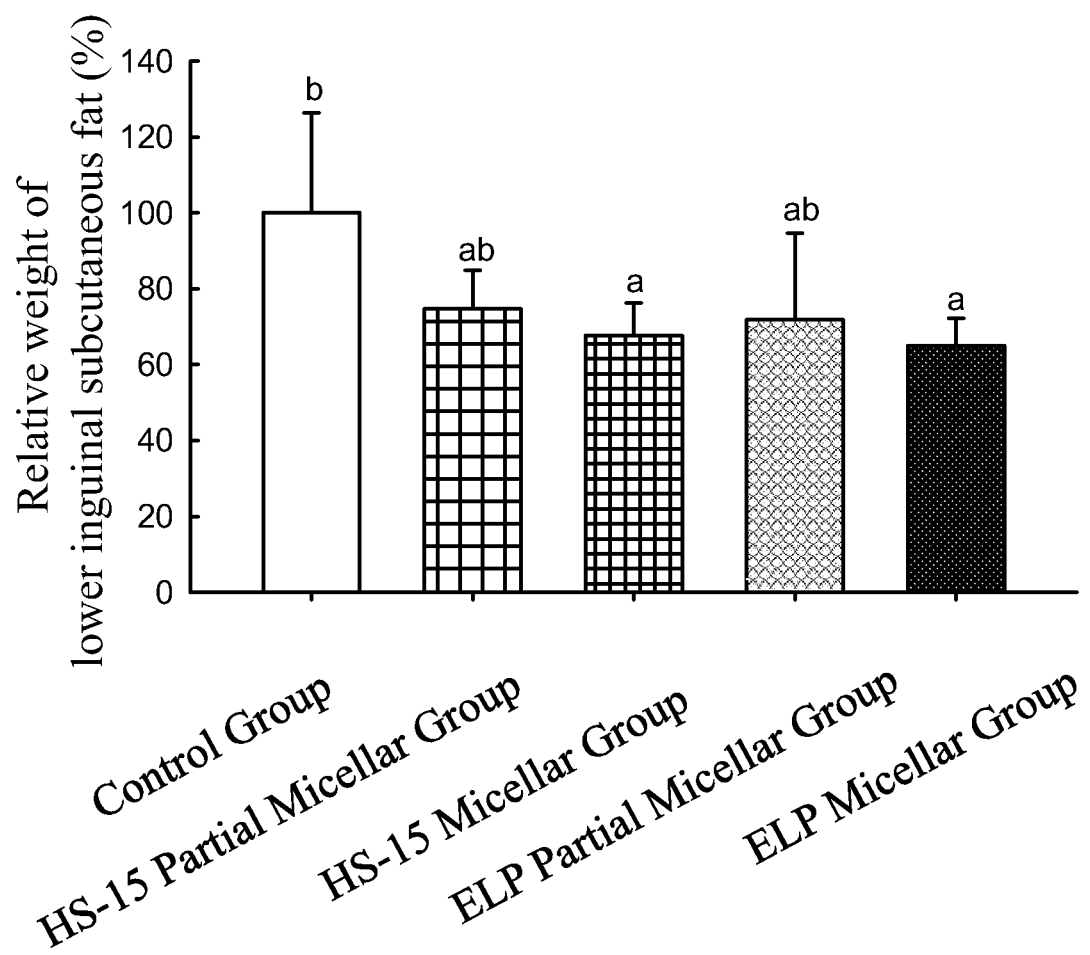
FIG. 3: A bar graph showing the effects of micelles on the amount of localized subcutaneous fat of rats.

Please refer to FIG. 3. FIG. 3 is a bar graph showing the effect of micelles on the amount of localized subcutaneous fat of rats. In FIG. 3, the y-axis is the relative weight of the lower inguinal subcutaneous fat (%), and the x-axis from left to right is the control group, the HS-15 partial micellar group, the HS-15 micellar group, the ELP partial micellar group, and the ELP micellar group, respectively.

As shown in FIG. 3, the relative weight of the lower inguinal subcutaneous fat of rats in the control group was 100.0±26.4%, the relative weight of the lower inguinal subcutaneous fat of rats in the HS-15 partial micellar group was 74.7±10.1%, the relative weight of the lower inguinal subcutaneous fat of rats in the HS-15 micellar group was 67.6±8.6%, the relative weight of the lower inguinal subcutaneous fat of rats in the ELP partial micellar group was 71.8±22.9%, and the relative weight of the lower inguinal subcutaneous fat of rats in the ELP micellar group was 65.0±7.2%.

Comparing to rats in the control group, rats in the HS-15 partial micellar group and the ELP partial micellar group showed a trend of reduction in their relative weights of the lower inguinal subcutaneous fat, but the difference did not reach statistical significance. The relative weights of lower inguinal subcutaneous fat of rats in the HS-15 micellar group and the ELP micellar group decreased significantly ($p<0.05$) by 32.4% and 35%, respectively.

The data above demonstrated that although the concentration of non-ionic surfactant and the concentration of curcumin in the partial micellar formations were identical to those of the micellar formations, and that the partial micellar formations contain some micelles, the partial micellar formations can only promote a trend of reduction of the localized fat but cannot significantly reduce the localized fat. On the contrary, the micellar formations with numerous micelles can significantly reduce the localized fat.

This demonstrated that formation of drug-containing micelles is a critical factor for curcumin compositions to significantly reduce the localized fat at the administration site. That is, curcumin compositions comprise few drug-containing micelles can induce a trend of localized fat reduction, and curcumin compositions with numerous drug-containing micelles can significantly reduce the localized fat.

Figure 4:
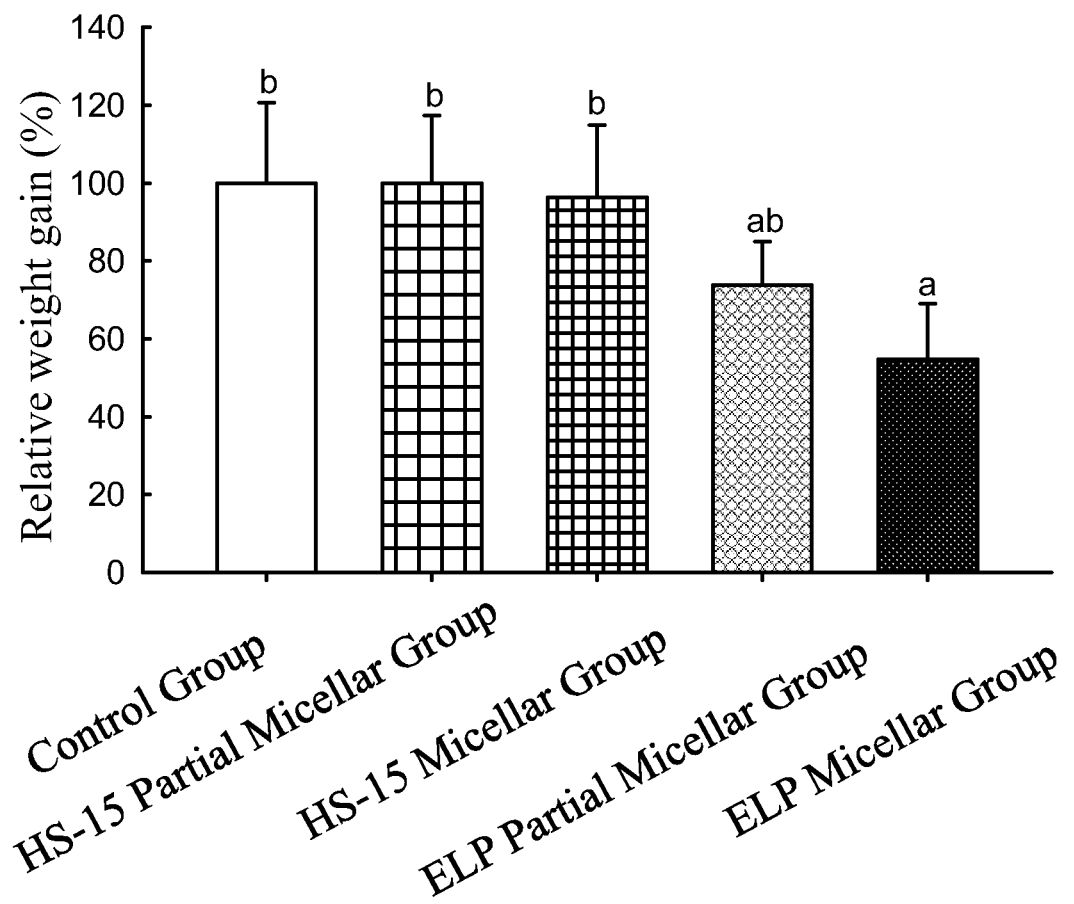
FIG. 4: A bar graph showing the effects of micelles on total body weight gain of rats.

Please refer to FIG. 4. FIG. 4 is a bar graph showing the effects of micelles on total body weight gain of rats. In FIG. 4, the y-axis is relative weight gain (%), and the x-axis from left to right is the control group, the HS-15 partial micellar group, the HS-15 micellar group, the ELP partial micellar group, and the ELP micellar group, respectively.

FIG. 4 shows that the relatively weight gain of rats in the control group is 100.0±20.6%, the relatively weight gain of rats in the HS-15 partial micellar group is 100.0±17.3%, the relatively weight gain of rats in the HS-15 micellar group is 96.4±18.5%, the relatively weight gain of rats in the ELP partial micellar group is 73.8±11.2%, and the relatively weight gain of rats in the ELP micellar group is 54.8±14.3%.

Comparing to rats in the control group, rats in the ELP partial micellar group showed a trend of reduction in their relative weight gain but the difference did not reach statistical significance ($p>0.05$). The relative weight gain of rats in the ELP micellar group was reduced by 45.2%, and was significantly different from that of the control group ($p<0.05$).

The data above showed that although the concentration of non-ionic surfactant and the concentration of curcumin in the partial micellar formations were identical to those of the micellar formations, and that the partial micellar formations contained some micelles, the partial micellar formations can only induce a trend of reduction of the body weight but not significantly reduce the body weight. On the contrary, the micellar formations with numerous micelles can significantly reduce the body weight.

This demonstrated that formation of drug-containing micelles is a critical factor for curcumin compositions to significantly reduce the body weight. That is, curcumin compositions with few drug-containing micelles can promote a trend of body weight loss, and curcumin compositions with numerous drug-containing micelles can significantly reduce the body weight.

Although the HS-15 micellar formulation did not significantly reduce the body weight in this experiment, based on the experiences of the inventor, the HS-15 micellar formulation can also significantly reduce the body weight if dosing frequency or administered dosage is increased. Therefore, the non-ionic surfactant HS-15 should also be included in the scope of the present invention.

Experiment 4: Preparation of the Pharmaceutical Compositions of the Present Invention The experiments above demonstrated that using non-ionic surfactants to form micelles is the critical factor for curcumin compositions to significantly reduce localized fat. Therefore, the present invention provides a simple curcumin pharmaceutical composition for reducing localized fat, and its characteristics is that the curcumin simple pharmaceutical composition comprises drug-containing micelles.

Preparation of the curcumin simple pharmaceutical composition is as follows:
(a) Mixing a first weight of curcumin with a solvent, and stirring at 150~500 rpm at room temperature until curcumin dissolves completely;
(b) Adding a second weight of a pharmaceutically acceptable surfactant, and stirring well at 100~300 rpm to volatilize the solvent. Wherein, the hydrophilic-lipophilic balance value (HLB value) of the surfactant is greater than 10; and
(c) Once the solvent volatilizes completely, slowly adding a third weight of a pharmaceutically acceptable aqueous solution to obtain drug-containing micelles; and
(d) Filtering through a 0.2 um filter, and storing the filtered solution comprising drug-containing micelles in dark and refrigeration;

Wherein, in step (c), the drug-containing micelle is a microstructure formed by the surfactant, and curcumin is encapsulated in said drug-containing micelle; the third weight is greater than or equal to 0 g.

Preferably, the operating procedure of step (c) is: Once the solvent volatilizes completely, slowly adding the third weight of the pharmaceutically acceptable aqueous solution, and mixing well to form drug-containing micelles.

Preferably, in step (a), the boiling point of the solvent is lower than that of pure water.

Preferably, in step (a), the solvent is a hydrophilic solvent.

Preferably, the hydrophilic solvent is at least one of methanol, ethanol, acetone, and other hydrophilic solvents, or combination thereof.

Preferably, the solvent in step (a) is a lipophilic (hydrophobic) solvent.

Preferably, the lipophilic (hydrophobic) solvent is at least one of ether, benzene, chloroform, ethyl acetate, dichloromethane, hexane, and other lipophilic (hydrophobic) solvents, or combination thereof.

Preferably, in step (b), the surfactant is a non-ionic surfactant.

Preferably, the non-ionic surfactant is at least one of polysorbate 80 (TWEEN® 80), polyoxyl 15 hydroxystearate (SOLUTOL® HS 15), polyoxyethylene castor oil derivatives, and other non-ionic surfactants, or combination thereof.

Preferably, the polyoxyethylene castor oil derivative is at least one of KOLLIPHOR® ELP (also known as CREMOPHOR® ELP, polyoxyl 35 castor oil), CREMOPHOR® RH 40 (polyoxyl 40 hydrogenated castor oil), and other polyoxyethylene castor oil derivatives, or combination thereof.

Preferably, in steps (a) and (b), the weight ratio of the curcumin of the first weight and the surfactant of the second weight is 1:5 to 1:500.

Preferably, in steps (a) and (b), the weight ratio of the curcumin of the first weight and the surfactant of the second weight is 1:20 to 1:150.

Preferably, in steps (a) and (c), the weight ratio of the curcumin of the first weight and the pharmaceutically acceptable aqueous solution of the third weight is 1:400 to 3:50.

Preferably, in step (c), the pharmaceutically acceptable aqueous solution is water for injection, aqueous solution for injection, or normal saline.

Preferably, in step (c), the pharmaceutically acceptable aqueous solution comprises a local anesthetic.

Preferably, in step (c), the pharmaceutically acceptable aqueous solution comprises an antioxidant.

Experiment 5: Determination of the Quality of Pharmaceutical Compositions

Experiment 5-1: Composition Analysis

Letting the pharmaceutical composition stand for at least 20 minutes. If the composition does not have stratification, further analyzing it by a particle analyzer.

Determining whether the pharmaceutical composition comprises micelles by a particle size analyzer. If the particle diameter of the pharmaceutical composition, after being analyzed by a particle analyzer, is smaller than 250 nm and the PDI value is less than 0.4, the solution of the pharmaceutical composition is deemed clear and transparent when observed by the naked eye, and the light beam can be observed when the solution of the pharmaceutical composition is shined by a laser, then it indicates that the pharmaceutical composition comprises micelles.

If micelles are present in the pharmaceutical composition, the prepared pharmaceutical composition is the pharmaceutical composition for reducing localized fat in the present invention.

Preferably, if the pharmaceutical composition does not have stratification and does not contain precipitates after being let stand, the prepared pharmaceutical composition is the preferable pharmaceutical composition of the present invention.

Experiment 5-2: Determination of the Stability of Pharmaceutical Compositions by Analyzing the Distribution of Particle Diameters Using a particle size analyzer (purchased from Malvern) to determine the distribution of particle diameters and the polydispersity index (PDI). If PDI is less than 0.4, it indicates that the stability of pharmaceutical composition is good, that is, the micelles in the pharmaceutical composition can exist stably.

Experiment 5-3: Determination of the Stability of Pharmaceutical Compositions by Accelerated Stability Test The storage condition of the pharmaceutical composition of the present invention is 2~8° C. In order to test the stability of the pharmaceutical compositions, the inventor placed the pharmaceutical compositions in an environment of relatively high temperature and relatively high humidity (temperature 25° C.±2° C., relative humidity 60%±5%) for accelerated stability test, observed how long the micelles in the pharmaceutical composition can stably exist in a condition of relatively high temperature, to reckon the shelf life of the pharmaceutical composition at 2~8° C. based on the accelerated stability test equation, as detailed below.

If the pharmaceutical composition has a shelf life of n months at a condition of 25° C., then the shelf life of the pharmaceutical composition at a condition of 5° C. is $2^{((25-5)/10)}$ folds of n months. That is, the shelf life of the pharmaceutical composition at a condition of 5° C. is $2^2$ folds of n months, that is, 4 folds.

For example, if the shelf life of the pharmaceutical composition is 6 months at a condition of 25° C., then the shelf life of the pharmaceutical composition at a condition of 5° C. is 24 months (6 months×4 folds=24 months.)

Preferably, the pharmaceutical composition maintains at a state without precipitation for at least 24 hours when it is subjected to accelerated stability test at a condition of temperature of 25° C.±2° C., relatively humidity of 60%±5%, and in the absence of direct light.

Preferably, the pharmaceutical composition maintains at a state without precipitation for at least 6 months when it is subjected to accelerated stability test at a condition of temperature of 25° C.±2° C., relatively humidity of 60%±5%, and in the absence of direct light.

Preferably, the pharmaceutical composition maintains at a state without precipitation for at least 24 months at a condition of temperature of 2~8° C.

Experiment 6: Maximum Drug Loading of Drug-Containing Micelles Formed by Different Non-Ionic Surfactants Because the maximum drug loading of drug-containing micelles directly affects injected volume, it has huge impacts on the volume of drug, side effects, and the burden that have to be tolerated by localized subcutaneous fat layer (e.g. the subcutaneous fat layer of the face) in a single administration. Thus, this experiment investigates the maximum drug loading of drug-containing micelles formed by different non-ionic surfactants to determine which non-ionic surfactant is the best excipient for preparing the pharmaceutical compositions of the present invention.

Four non-ionic surfactants were selected for this experiment. The four non-ionic surfactants were KOLLIPHOR® ELP (also known as CREMOPHOR® ELP (polyoxyl 35 castor oil, abbreviated as ELP), KOLLIPHOR® HS-15 (HS-15), CREMOPHOR® RH 40 (polyoxyl 40 hydrogenated castor oil, abbreviated as RH 40), and polysorbate 80 (also known as TWEEN® 80).

The experiment was divided into 4 groups, which were an ELP group, a HS-15 group, a RH40 group, and a TWEEN® 80 group.

EXPERIMENTAL PROCEDURE (a') 2.0 g (an example of the first weight) of curcumin was mixed with 300~500 mL of dichloromethane, and stirred at 150~500 rpm at room temperature until curcumin dissolved completely.

(b') 18.0 g (an example of the second weight) of one of the non-ionic surfactants mentioned above was added to the solution, and stirred at 100~300 rpm to volatilize dichloromethane; and (c') A composition of 20 g in total was obtained after the solvent volatilized completely; 2 g of the composition was weighed out, and 8 g (an example of the third weight) of normal saline for injection was added and mixed well to obtain a composition to be tested. The concentration of curcumin in the composition to be tested was 20 mg/g, and the concentration of the non-ionic surfactant was 18%.

The compositions to be tested from the ELP group, the HS-15 group, the RH40 group, and the TWEEN® 80 group were let stand for at least 20 minutes to observe if stratification occurs. If stratification occurs, it indicates that the concentration of curcumin is too high and will cause the micelles in the composition to be tested to burst. That is, the non-ionic surfactant cannot be used to prepare the pharmaceutical compositions of the present invention which comprise as high as 20 mg/g of curcumin.

The experimental results showed that the compositions to be tested in the HS-15 group and the RH40 group had stratification, and only the compositions to be tested from the ELP group and the TWEEN® 80 group did not have stratification. Therefore, the maximum drug loading of drug-containing micelles formed by HS-15 and RH40 are both smaller than 20 mg/g. The drug-containing micelles formed by ELP and TWEEN® 80 can be used to prepare pharmaceutical compositions with 20 mg/g of curcumin.

Because TWEEN® 80 is toxic, different national pharmacopoeias all limit the injection concentration of TWEEN® 80 to less than 0.4% to avoid adverse effects or toxicity. Thus, the maximum drug loading of the drug-containing micelles formed by TWEEN® 80 should be 0.44 mg/g. (Calculation: 20 mg/g×(0.4%/18%)=0.44 mg/g.)

In order to determine the maximum drug loading of ELP, the inventor further performed Experiment 6 and determined that the maximum drug loading of ELP is greater than or equal to 111 mg/g. (When the ratio of curcumin to ELP is 1:8, the prepared pharmaceutical composition contains 111 mg/g of curcumin.)

The results above indicated that ELP is the best excipient to prepare the pharmaceutical compositions of the present invention. The concentration of curcumin can reach 111 mg/g in the pharmaceutical compositions prepared with ELP, while the concentration of curcumin is less than 20 mg/g in the pharmaceutical compositions prepared with other non-ionic surfactants (please refer to Table 1).

In order to determine which of the non-ionic surfactants between HS-15 and RH40 has the minimum drug loading, the inventor further used those non-ionic surfactants to prepare the pharmaceutical compositions of the present invention with 10 mg/g of curcumin. The results showed that ELP, HS-15, RH40, and TWEEN® 80 can all be used to prepare the pharmaceutical compositions of the present invention with 10 mg/g of curcumin, and said pharmaceutical compositions of the present invention with 10 mg/g of curcumin were clear without stratification, and the measured particle diameters were 15.95±0.24 nm, 88.23±116.06 nm, 21.63±9.34 nm, 11.37±0.13 nm, respectively, and the PDI values were 0.32±0.02, 0.48±0.27, 0.26±0.09, 0.33±0.04, respectively.

Wherein, when HS-15 was used to prepare the pharmaceutical composition of the present invention with 10 mg/g of curcumin, the PDI value of the prepared pharmaceutical composition was greater than 0.4, and it did not satisfy the definition of the presence of micelles in the pharmaceutical composition of the present invention (measured particle diameter is smaller than 250 nm, PDI value is less than 0.4, the solution of the pharmaceutical composition is deemed clear and transparent when it is observed by the naked eye, and light beam can be observed when the solution of the pharmaceutical composition is shined by a laser.) Therefore, among the non-ionic surfactants selected for this experiment, HS-15 has the minimum drug loading.

TABLE 1

Maximum drug load of drug-containing micelles formed by different non-ionic surfactants

| Group | Maximum drug load of the micelles (mg/g) | Maximum tolerated dosage of micellar drug load |
|---|---|---|
| ELP group | ≥111 | ≥111 |
| HS-15 group | <10 | <10 |
| RH40 | <20; ≥10 | <20; ≥10 |
| Tween ® 80 | ≥20 | 0.44 |

Experiment 6: Preparation of Pharmaceutical Compositions with KOLLIPHOR® ELP (ELP)

In order to determine both of the appropriate ratio between curcumin and KOLLIPHOR® ELP (ELP) and the maximum drug loading when preparing the pharmaceutical compositions in the present invention with ELP, various ratios between curcumin and KOLLIPHOR® ELP (also known as CREMOPHOR® ELP, polyoxyl 35 castor oil abbreviated as ELP) were used in this experiment to prepare a series of pharmaceutical compositions of the present invention, and the stability analysis thereof were performed.

There were 9 groups in this experiment, that is, the first to the ninth group. The preparation of pharmaceutical composition in each group was roughly the same as the experimental procedure in Experiment 5. The only differences were the weight of curcumin (the first weight in step (a')), the weight of ELP (the second weight in step (b')), and the weight of normal saline for injection (the third weight in step (c')). In this experiment, the guideline of adding all of the weight of curcumin (the first weight), the weight of ELP (the second weight), and the weight of normal saline for injection (the third weight) was shown in Table 2.

In this experiment, the ratios of curcumin to ELP (weight ratio) in the first group to the ninth group were 1:4, 1:5, 1:8, 1:10, 1:20. 1:40, 1:100, 1:150, 1:500, respectively, and the final concentrations of curcumin in the pharmaceutical compositions prepared in the first to the ninth group were 200 mg/g, 167 mg/g, 111 mg/g, 91 mg/g, 47.62 mg/g, 7.5 mg/g, 3 mg/g, 2 mg/g, and 0.5 mg/g, respectively. That is, the preparation method of pharmaceutical composition in the first to the ninth group, the weight ratios of curcumin in step (a') to ELP in step (b') (the ratios of the first weight to the second weight) were 1:4, 1:5, 1:8, 1:10, 1:20. 1:40, 1:100, 1:150, 1:500, respectively, and that after adding the third weight of normal saline for injection in step (c'), the final concentrations of curcumin in the prepared pharmaceutical compositions were 200 mg/g, 167 mg/g, 111 mg/g, 91 mg/g, 47.62 mg/g, 7.5 mg/g, 3 mg/g, 2 mg/g, and 0.5 mg/g, respectively. Wherein, when the final concentration of drug was presented as mg/g, it indicated the number of milligrams of curcumin per gram of pharmaceutical composition.

Particle size analyzer was utilized to determine if micelles were present in the pharmaceutical compositions, and the particle diameter of the micelles was measured.

To assess the stability of the pharmaceutical compositions, the distribution of particle diameters and the polydispersity index (PDI) were measured by a particle size analyzer. The curcumin content in the micelles was analyzed by high performance liquid chromatography (HPLC; e.g., HPLC-UV) and defined as the "initial drug content".

TABLE 2

A sample preparation chart for preparing pharmaceutical compositions with ELP

| Group | Ratio of curcumin to ELP (weight ratio) | Final concentration of curcumin in the pharmaceutical composition (mg/g) |
|---|---|---|
| 1 | 1:4 | 200 |
| 2 | 1:5 | 167 |
| 3 | 1:8 | 111 |
| 4 | 1:10 | 91 |
| 5 | 1:20 | 47.62 |
| 6 | 1:40 | 7.5 |
| 7 | 1:100 | 3 |
| 8 | 1:150 | 2 |
| 9 | 1:500 | 0.5 |

The pharmaceutical compositions were subjected to accelerated stability test to observe if stratification occurred when the pharmaceutical compositions were stored at high temperature storage condition (25±2° C.) for 3 months. The drug content in the micelles was determined by high performance liquid chromatography (HPLC; e.g., HPLC-UV), and defined as the "drug content after accelerated stability test". The "percentage of drug content" was calculated by dividing the "drug content after accelerated stability test" by the "initial drug content". If the percentage of drug content is greater than or equal to 95%, it indicates that the stability of the pharmaceutical composition is excellent.

Please refer to Table 3. Table 3 is the stability analysis result of the pharmaceutical compositions. Table 3 shows the presence of micelles in the second to the ninth pharmaceutical compositions. Therefore, pharmaceutical compositions prepared with curcumin to ELP ratios of 1:5 to 1:500 are all pharmaceutical compositions for reducing localized fat in the present invention.

In terms of stability, when the ratios of curcumin to ELP were 1:4 and 1:5, PDI was greater than 0.4. When the ratios of curcumin to ELP were 1:8 to 1:500, PDI was smaller than 0.4. Thus, in order to prepare the pharmaceutical composition for reducing localized fat in the present invention with better stability, the ratio of curcumin to ELP should be less than one-fifth (⅕). That is, in order to prepare the pharmaceutical composition for reducing localized fat in the present invention with better stability, based on 1 weight unit defined as the weight of curcumin, the weight of ELP should be greater than 5 weight units. Preferably, based on 1 weight unit defined as the weight of curcumin, the weight of ELP is 8~500 weight units. Preferably, based on 1 weight unit defined as the weight of curcumin, the weight of ELP is 20~150 weight units.

Based on the data in Table 3, when the pharmaceutical compositions in the fifth to the eighth group were stored at 25° C. for 3 months, the percentage of curcumin drug content in every sample was greater than 95% and did not show a significant trend of decrease comparing to the initial drug content. This result indicates that the pharmaceutical compositions have excellent stability, and based on the equation of accelerated stability test, the pharmaceutical compositions can be stored at 2~8° C. in refrigeration for at least 24 months.

Experiment 7: The Effects of Curcumin-Resveratrol Complex Subcutaneous Injection Formulation on the Subcutaneous Fat of Rats Experiment 7-1: The Effects of Resveratrol Simple Subcutaneous Injection Formulation on the Subcutaneous Fat of Rats Preparation of the Resveratrol Subcutaneous Injection Formulation:

Resveratrol was mixed with an appropriate amount of normal saline for injection to obtain the resveratrol subcutaneous injection formulation.

Rats were assigned into a high-fat diet control group and a resveratrol group with 6 rats per group. The rats were fed in the same manner described in Experiment 2. The resveratrol subcutaneous injection formulation was injected to the lower inguinal subcutaneous fat layer of rats in the resveratrol group, and each injected dosage was 8 mg of resveratrol per kilogram of body weight (8 mg/kg). Rats in the high-fat diet control group were injected with the same volume of water for injection in the same manner described above.

The injection sites mentioned above were the lower inguinal fat pads of rats. Bilateral injections were administered evenly once a day on day 1, 3, and 5 of the experiment. The rats were fed with high-fat diet for the entire duration of the experiment. Their weight changes were recorded daily, and food and water consumption was recorded weekly. The experiment lasted for 20 days, and the rats were euthanized on day 21 by $CO_2$.

Figure 5:
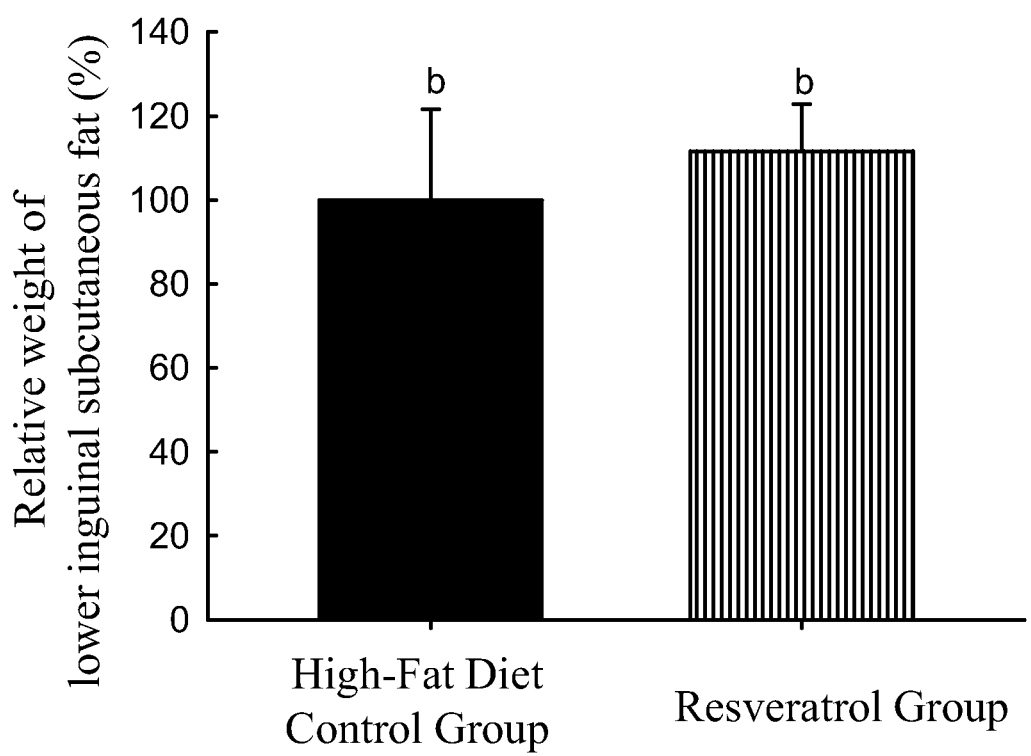
FIG. 5: A bar graph showing the effects of resveratrol subcutaneous injection formulation without excipient on the amount of localized subcutaneous fat of rats.

Please refer to FIG. 5. FIG. 5 is a bar graph showing the effects of resveratrol subcutaneous injection formulation without excipient on the amount of localized subcutaneous fat of rats Results from FIG. 5 showed that the relative weight of the lower inguinal subcutaneous fat of rats in the high-fat diet control group was 100.00±21.51%, and the relative weight of the lower inguinal subcutaneous fat of rats in the resveratrol group was 111.59±11.288%. There was no significant difference in the relative weight of the lower inguinal subcutaneous fat between rats in the resveratrol group and rats in the high-fat diet control group, indicating that a lipophilic plant extract-resveratrol composition without excipient cannot reduce the fat at the administration site (localized fat). Therefore, the inventor believed that directly mixing resveratrol and curcumin and injecting into the subcutaneous fat may not be able to reduce localized fat, so

TABLE 3

Stability analysis of the pharmaceutical compositions

| Group | Ratio of curcumin to ELP (weight ratio) | Micelle particle diameter (nm) | PDI | Appearance after accelerated stability test | Drug content after accelerated stability test |
|---|---|---|---|---|---|
| 1 | 1:4 | 772.5 ± 198.92 | 0.79 ± 0.36 | | |
| 2 | 1:5 | 153.97 ± 40.17 | 0.41 ± 0.13 | | |
| 3 | 1:8 | 13.17 ± 0.21 | 0.2 ± 0.02 | | |
| 4 | 1:10 | 12.47 ± 0.23 | 0.17 ± 0.01 | | |
| 5 | 1:20 | 12.57 ± 0.12 | 0.137 ± 0.03 | Clear without stratification | 103.82 ± 2.07 |
| 6 | 1:40 | 11.59 ± 0.27 | 0.174 ± 0.0 | Clear without stratification | 100.78 ± 0.51 |
| 7 | 1:100 | 12.26 ± 0.12 | 0.096 ± 0.07 | Clear without stratification | 100.62 ± 0.21 |
| 8 | 1:150 | 12.93 ± 0.29 | 0.197 ± 0.02 | Clear without stratification | 102.45 ± 0.05 |
| 9 | 1:500 | 12.66 ± 0.14 | 0.16 ± 0.01 | | |

In the table above, blank cells indicate that the contents were not analyzed.

the inventor further investigated if excipients can improve the local lipolysis efficacy of a complex drug (resveratrol+curcumin).

Experiment 7-2: The Effect of Curcumin-Resveratrol Complex Formula with Excipient on the Subcutaneous Fat of Rats A curcumin-resveratrol complex solution comprising formulation A and a curcumin-resveratrol complex solution comprising ELP were prepared as follows:

Preparation of the curcumin-resveratrol complex solution comprising formulation A: 0.05 g of resveratrol, 0.2 g of curcumin, and 2 g of mannitol were grinded and mixed well to obtain a powder formulation. 0.05 g of carboxymethylcellulose (CMC) was mixed with 40 mL of sterile water and heated to 60° C.~70° C. to dissolve carboxymethylcellulose (CMC), and 0.055 g of polysorbate 80 (TWEEN® 80) was added and mixed well until it dissolved completely. Water was added to a total volume of 50 mL to obtain a liquid formulation. The liquid formulation was added into the powder formulation and mixed well to obtain the curcumin-resveratrol complex solution comprising formulation A. Said formulation A was TWEEN® 80 with mannitol. Said curcumin-resveratrol complex solution comprising formulation A did not comprise micelles, the concentration of curcumin was 4 mg/mL, and the concentration of resveratrol was 1 mg/mL.

Preparation of the Curcumin-Resveratrol Complex Solution Comprising ELP:

0.2 g of resveratrol, 0.8 g of curcumin, and 150~200 mL of dichloromethane were mixed together, and stirred at 150~500 rpm at room temperature until curcumin dissolved completely. 40 g of KOLLIPHOR® ELP (also known as CREMOPHOR® ELP, polyoxyl 35 castor oil, abbreviated as ELP) was added and stirred at 100~300 rpm to volatilize dichloromethane. Once dichloromethane volatilized completely, normal saline for injection was slowly added to a total volume of 200 mL. The solution was mixed well to obtain a curcumin-resveratrol complex solution comprising ELP. Said curcumin-resveratrol complex solution comprising ELP comprised micelles, the concentration of KOLLIPHOR® ELP (ELP) was approximately 20%, and the weight ratio of curcumin, resveratrol, and ELP was 4:1:200.

The rats were randomly assigned into 4 groups, which were a high-fat diet control group, a low-dosage complex formula with formulation A group, a high-dosage complex formula with formulation A group, and a low-dosage complex formula with ELP group. The rats were fed in the same manner described in Experiment 2.

The curcumin-resveratrol complex solution comprising formulation A was injected to the inguinal subcutaneous fat layer of rats in the low-dosage complex formula with formulation A group, and each injection volume was 0.2 ml of the curcumin-resveratrol complex solution comprising formulation A per kilogram of body weight (0.2 mL/kg), such that each injected dosage was 1 mg of curcumin-resveratrol complex formula per kilogram of body weight (1 mg/kg); the curcumin-resveratrol complex solution comprising formulation A was injected to the inguinal subcutaneous fat layer of rats in the high-dosage complex formula with formulation A group, and each injection volume was 1 mL of the curcumin-resveratrol complex solution comprising formulation A per kilogram of body weight, such that each injected dosage was 5 mg of curcumin-resveratrol complex formula per kilogram of body weight (5 mg/kg); the curcumin-resveratrol complex solution comprising ELP was injected to the inguinal subcutaneous fat layer of rats in the low-dosage complex formula with ELP group, and each injection volume was 0.2 mL of the curcumin-resveratrol complex solution comprising ELP per kilogram of body weight (0.2 mL/kg), such that each injected dosage was 1 mg of curcumin-resveratrol complex formula per kilogram of body weight (1 mg/kg). Rats in the high-fat diet control group were injected with the same volume of normal saline for injection in the same manner described above.

The injection sites mentioned above were the lower inguinal fat pads of rats. Bilateral injections were administered evenly once a day on day 1, 3, and 5 of the experiment. The rats were fed with high-fat diet for the entire duration of the experiment. The experiment lasted for 20 days, and the rats were euthanized on day 21 by $CO_2$.

Figure 6:
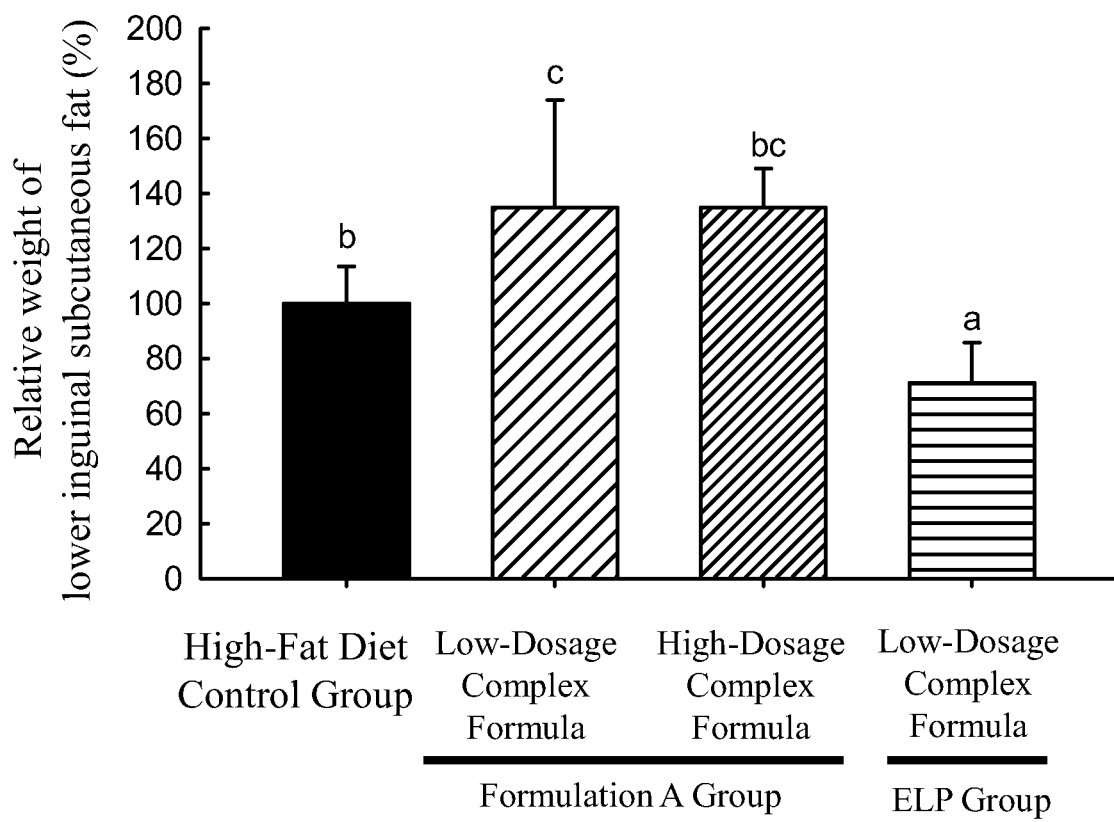
FIG. 6: A bar graph showing the effects of curcumin-resveratrol complex subcutaneous injection formulations prepared with different excipients on the amount of localized subcutaneous fat of rats.

Please refer to FIG. 6. FIG. 6 is a bar graph showing the effects of curcumin-resveratrol complex subcutaneous injection formulations prepared with different excipients on localized subcutaneous fat of rats.

Results in FIG. 6 showed that the relative weight of the lower inguinal subcutaneous fat of rats in the high-fat diet control group was 100.0±13%, the relative weight of the lower inguinal subcutaneous fat of rats in the low-dosage complex formula with formulation A group was 134.9±39%, the relative weight of the lower inguinal subcutaneous fat of rats in the high-dosage complex formula with formulation A group was 134.9±14%, and the relative weight of the lower inguinal subcutaneous fat of rats in the low-dosage complex formula with ELP group was 71.1±14%. Comparing to the high-fat diet control group, neither the low-dosage complex formula with formulation A group nor high-dosage complex formula with formulation A group can reduce the fat at the administration site (localized fat) ($p>0.05$).

The relative weight of the lower inguinal subcutaneous fat of rats in the low-dosage complex formula with ELP group was significantly different from that of rats in the control group ($p<0.05$), and the relative weight of the lower inguinal subcutaneous fat of rats in the low-dosage complex formula with ELP group was reduced by 28.9%. Based on the preparation described above, the curcumin-resveratrol complex solution comprising ELP administered to the group comprises the drug-containing micelles (encapsulating curcumin) and the second lipophilic drug-containing micelles (encapsulating resveratrol). Therefore, similar to the curcumin simple pharmaceutical composition, formation of micelles is the critical factor for the curcumin-resveratrol complex solution comprising ELP to significantly reduce localized fat.

Experiment 7-3: Comparison Between Curcumin-Resveratrol Complex Pharmaceutical Composition and Simple Pharmaceutical Composition The curcumin simple pharmaceutical composition, the resveratrol simple pharmaceutical composition, and the curcumin-resveratrol complex pharmaceutical composition of the present invention were prepared as follows:

Preparation of the curcumin simple pharmaceutical composition: same as the preparation of the curcumin ELP solution described in Experiment 2. Wherein, the concentration of curcumin was 5 mg/mL.

Preparation of the Resveratrol Simple Pharmaceutical Composition:

approximately the same as the preparation of the curcumin ELP solution described in Experiment 2, only that curcumin was replaced by resveratrol. The concentration of resveratrol in the prepared resveratrol simple pharmaceutical composition was 5 mg/mL.

Preparation of the curcumin-resveratrol complex pharmaceutical composition: same as the preparation of the curcumin-resveratrol complex solution comprising ELP described in Experiment 7-2. Wherein, the total concentration of curcumin and resveratrol was 5 mg/mL, and the ratio of curcumin to resveratrol was 4:1.

The rats were assigned into a high-fat diet control group, a curcumin group, a resveratrol group, and a curcumin-resveratrol complex group, with 5 rats in each group. The rats were fed in the same manner described in Experiment 2.

The curcumin simple pharmaceutical composition, the resveratrol simple pharmaceutical composition, and the curcumin-resveratrol complex pharmaceutical composition were injected to the lower inguinal subcutaneous fat layer of rats in the curcumin group, the resveratrol group, and the curcumin-resveratrol complex group, respectively. Each injection volume was 2 mL per kilogram of body weight (2 mL/kg), such that each injected dosage was 10 mg of drug per kilogram of body weight (10 mg/kg). That is, rats in the curcumin group were administered with 10 mg of curcumin per kilogram of body weight; rats in the resveratrol group was administered with 10 mg of resveratrol per kilogram of body weight; rats in the curcumin-resveratrol complex group were administered with 8 mg of curcumin and 2 mg of resveratrol per kilogram of body weight. Rats in the high-fat diet control group were injected with a same volume of normal saline for injection in the same manner described above.

The injection sites mentioned above were the lower inguinal fat pads of rats. Bilateral injections were administered evenly once a day on day 1, 2, 3, and 4 of the experiment. The rats were fed with high-fat diet for the entire duration of the experiment. The experiment lasted for 14 days, and the rats were euthanized on day 15 by $CO_2$.

Because each group was administered with 10 mg/kg of drug each time, the local lipolysis efficacy of the curcumin-resveratrol complex group should be between that of the curcumin group and the resveratrol group. If the local lipolysis efficacy of the curcumin-resveratrol complex group is better than that of the curcumin group and the resveratrol group, it indicates that curcumin and resveratrol in the curcumin-resveratrol complex pharmaceutical composition manifests synergy in the local lipolysis efficacy.

Figure 7:
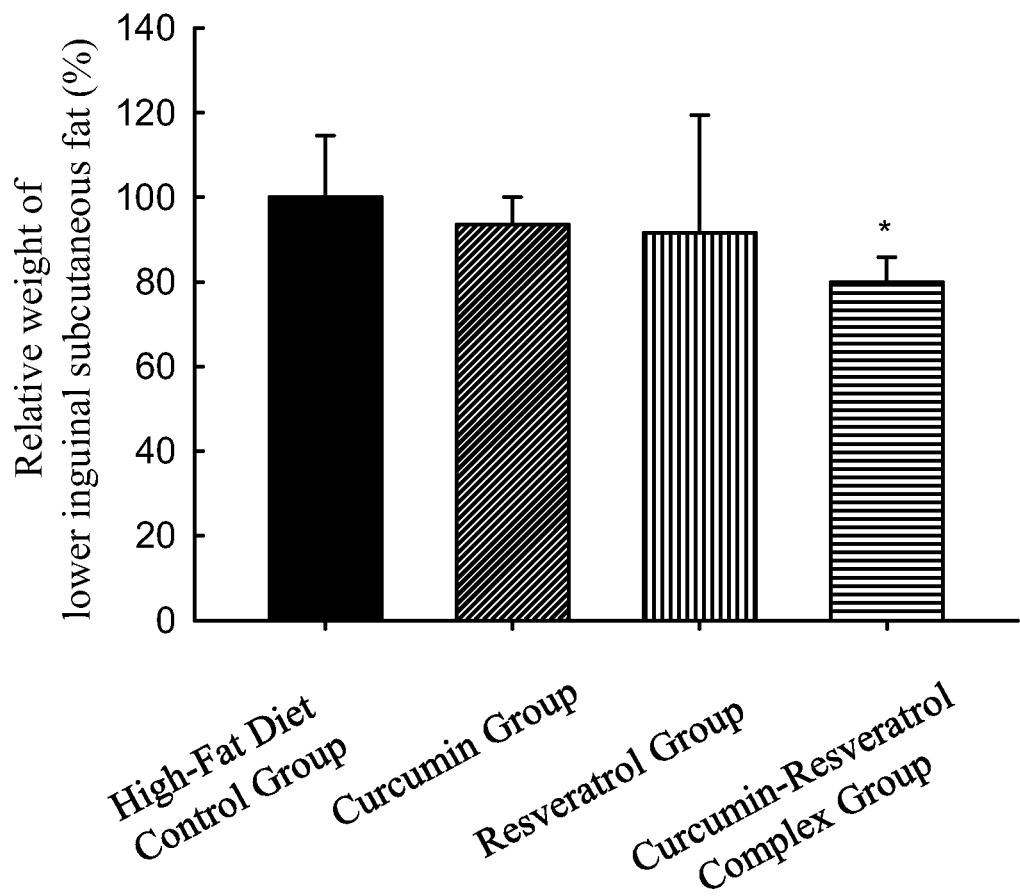
FIG. 7: A bar graph showing the effects of curcumin simple, resveratrol simple, and curcumin-resveratrol complex subcutaneous injection formulations comprising micelles on the amount of localized subcutaneous fat of rats.

Please refer to FIG. 7. FIG. 7 is a bar graph showing the effect of curcumin simple, resveratrol simple, and curcumin-resveratrol complex subcutaneous injection formulations comprising micelles on the amount of localized subcutaneous fat of rats.

Results in FIG. 7 showed that the relative weight of the lower inguinal subcutaneous fat in rats in the high-fat diet control group was 100.0±14.6%, the relative weight of the lower inguinal subcutaneous fat of rats in the curcumin group was 93.5±6.5%, the relative weight of the lower inguinal subcutaneous fat of rats in the resveratrol group was 91.6±27.8%, and the relative weight of the lower inguinal subcutaneous fat of rats in the curcumin-resveratrol complex group was 80.0±5.8%. Comparing to the high-fat diet control group, the curcumin or the resveratrol group cannot significantly reduce the fat at the administration site (localized fat) ($p>0.05$).

The relative weight of the lower inguinal subcutaneous fat of rats in the curcumin-resveratrol complex group was significantly different from that of rats in the high-fat diet control group ($p<0.05$), and the relative weight of the lower inguinal subcutaneous fat of rats in the curcumin-resveratrol complex group was reduced by 20%.

Comparison among the local lipolysis efficacy of the curcumin group, the resveratrol group, and the curcumin-resveratrol complex group demonstrated that curcumin and resveratrol in the curcumin-resveratrol complex group manifests synergy in the local lipolysis efficacy.

Experiment 7-4: The Effects of Dosing Frequency on the Subcutaneous Fat and the Body Weight of Rats In this experiment, rats in each group were administered with an equal amount of total injected dosage of the curcumin-resveratrol complex pharmaceutical composition but with different dosing frequency to assess the effect of dosing frequency on the subcutaneous fat and the body weight of rats. In this experiment, other rats were administered with the main ingredient of a local lipolysis injection formulation available in the market to simultaneously compare the effects of the curcumin-resveratrol complex pharmaceutical composition of the present invention and the local lipolysis injection formulation in the market on the subcutaneous fat and the body weight of rats.

A sodium deoxycholate solution and a curcumin-resveratrol complex pharmaceutical composition were prepared as follows:

Preparation of the sodium deoxycholate solution: An appropriate amount of sodium deoxycholate was mixed with sterile water for injection to make the concentration of sodium deoxycholate 2.575 mg/mL. The solution was mixed well to obtain the sodium deoxycholate solution. Wherein, sodium deoxycholate (purchased from Sigma-Aldrich, cat #D6750) is the main ingredient of the local lipolysis injection formulation ATX-101 (brand name: KYBELLA®) in the market.

Preparation of the curcumin-resveratrol complex pharmaceutical composition: same as the preparation of the curcumin-resveratrol complex solution comprising ELP described in Experiment 7-2. Wherein, the total concentration of curcumin and resveratrol was 5 mg/mL, and the ratio of curcumin to resveratrol was 4:1.

The rats were randomly assigned into 4 groups, which were a high-fat diet control group, a sodium deoxycholate group, a high-dosing frequency curcumin-resveratrol group (abbreviated as high-dosing frequency group in this experiment), and a low-dosing frequency curcumin-resveratrol group (abbreviated as low-dosing frequency group in this experiment). The rats were fed in the same manner described in Experiment 2.

The drugs were administered as follows:

The sodium deoxycholate group: The sodium deoxycholate solution was injected to the lower inguinal subcutaneous fat layer of rats in the sodium deoxycholate group. Each injection volume was 4 mL per kilogram of body weight (4 mL/kg), such that each injected dosage was 10.3 mg (10.3 mg/kg; calculation: 2.575 mg/mL×4 mL/kg=10.3 mg/kg). Rats were injected once a day on day 1, 3, and 5 of the experiment, with 3 injections in total, such that the total dosage was 30.9 mg/kg (10.3 mg/kg×3 times=30.9 mg/kg).

The high-dosing frequency group: The curcumin-resveratrol complex pharmaceutical composition was injected to the lower inguinal subcutaneous fat layer of rats in the high-dosing frequency group. Each injection volume was 4 mL per kilogram of body weight (4 mL/kg), such that each injected dosage was 20 mg (20 mg/kg; calculation: 5 mg/mL×4 mL/kg=20 mg/kg). Rats were injected once a day on day 1, 3, 5, 7, 9, and 11 of the experiment, with 6 injections in total, such that the total dosage was 120 mg/kg (20 mg/kg×6 times=120 mg/kg).

The low-dosing frequency group: The curcumin-resveratrol complex pharmaceutical composition was injected to the lower inguinal subcutaneous fat layer of rats in the low-dosing frequency group. Each injection volume was 8 mL per kilogram of body weight (8 mL/kg), such that each injected dosage was 40 mg (40 mg/kg; calculation: 5 mg/mL×8 mL/kg=40 mg/kg). Rats were injected once a day on day 1, 3, and 5 of the experiment, with 3 injections in total, such that the total dosage was 120 mg/kg (40 mg/kg×3 times=120 mg/kg).

The high-fat diet control group: rats were injected with water for injection in the same manner described above.

The rats were fed with high-fat diet for the entire duration of the experiment. The experiment lasted for 20 days, and the rats were euthanized on day 21 by $CO_2$.

Figure 8A:
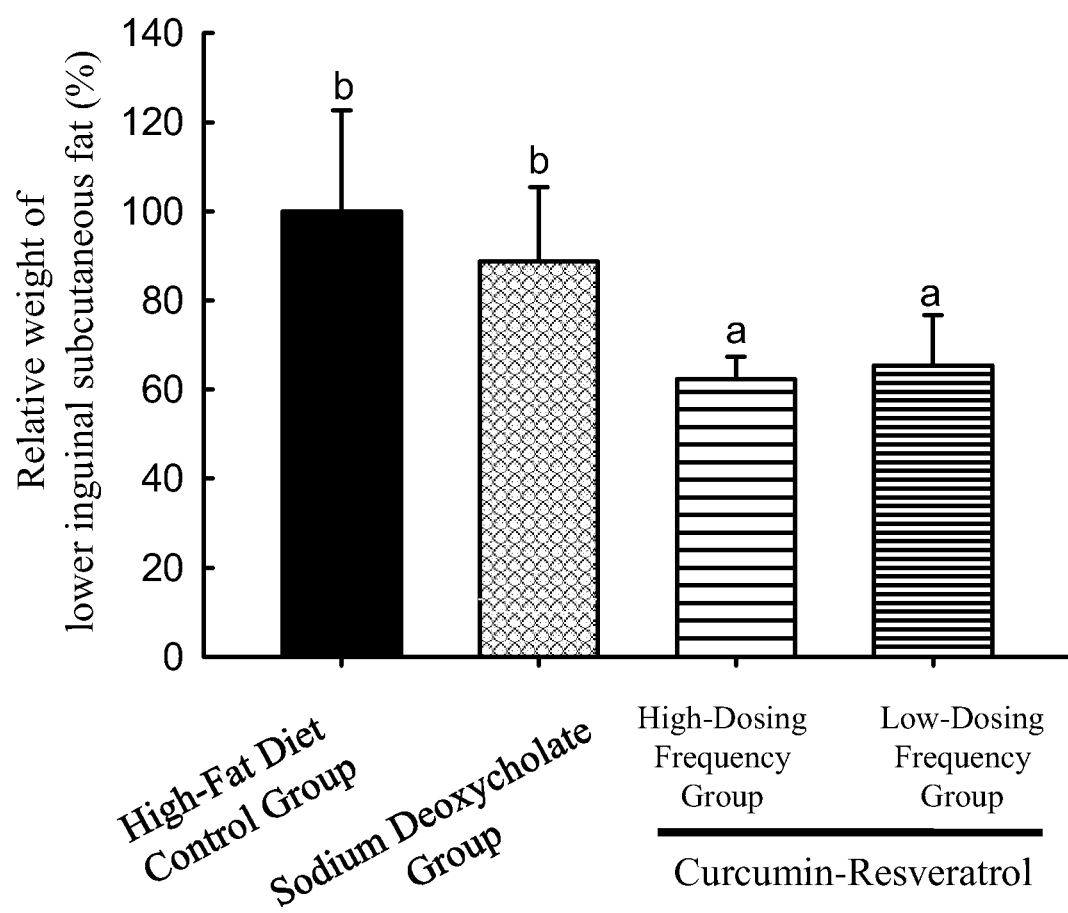
FIG. 8A: A bar graph showing the effects of dosing frequency of curcumin-resveratrol complex pharmaceutical composition on the amount of localized subcutaneous fat of rats.
Figure 8B:
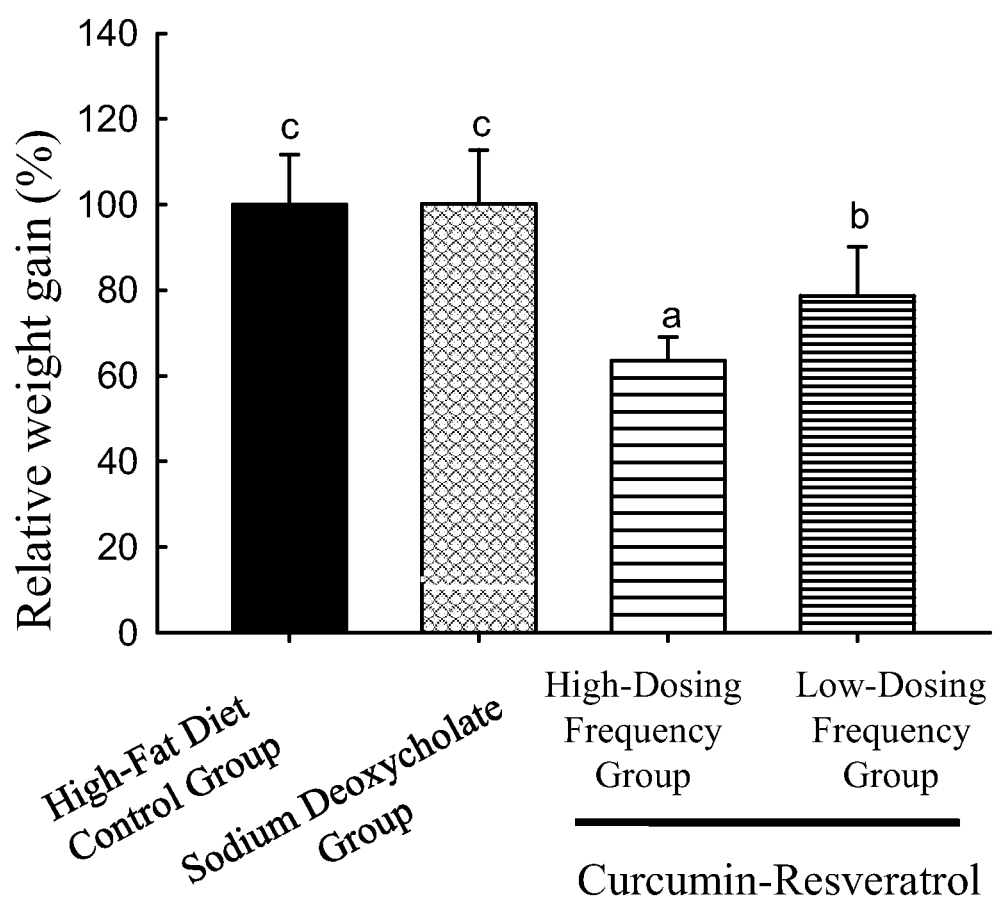
FIG. 8B: A bar graph showing the effects of dosing frequency of curcumin-resveratrol complex pharmaceutical composition on total body weight gain of rats.

Please refer to FIGS. 8A and 8B. FIG. 8A is a bar graph showing the effects of dosing frequency of the curcumin-resveratrol complex pharmaceutical composition on localized subcutaneous fat of rats. FIG. 8B is a bar graph showing the effects of dosing frequency of the curcumin-resveratrol complex pharmaceutical composition on total body weight gain of rats.

Results in FIG. 8A showed that the relative weight of the lower inguinal subcutaneous fat of rats in the high-dosing frequency group was 100.0±22.6%, the relative weight of the lower inguinal subcutaneous fat of rats in the sodium deoxycholate group was 88.8±16.7%, the relative weight of the lower inguinal subcutaneous fat of rats in the high-dosing frequency group was 62.3±5.1%, and the relative weight of the lower inguinal subcutaneous fat of rats in the low-dosing frequency group was 65.4±11.3%.

Comparing to the high-fat diet control group, both the high-dosing frequency group and the low-dosing frequency group can significantly reduce the fat at the administration site (localized fat) ($p<0.05$). Thus, if the concentration of the curcumin-resveratrol complex pharmaceutical composition is sufficient, low-dosing frequency can achieve the effect of local lipolysis.

Comparing to the low-dosing frequency group, the lipolysis effect of the high-dosing frequency group is better. Although there was no significant difference between high-dosing frequency and low-dosing frequency, the high-dosing frequency can achieve a better trend of local lipolysis effect.

Results in FIG. 8B showed that the relative weight gain in rats of the high-fat diet control group was 100.0±11.6%, the relative weight gain of rats in the sodium deoxycholate group was 100.2±12.6%, the relative weight gain of rats in the high-dosing frequency group was 63.5±5.5%, and the relative weight gain of rats in the low-dosing frequency group was 78.7±11.5%. Comparing to the relative weight gain of rats in the high-fat diet control group, the relative weight gain of rats in both the low-dosing frequency group and the high-dosing frequency group was significantly decreased ($p<0.05$), and the relative weight gain was decreased by 21.3% and 36.5%, respectively, showing that the weight loss effect was very significant.

Therefore, the curcumin-resveratrol complex pharmaceutical composition of the present invention can significantly reduce the body weight, and the weight loss efficacy of high-dosing frequency is significantly better than that of low-dosing frequency ($p<0.05$).

Based on the experiences of the inventor, when the dosing frequency suitable for rats is 3~6 times, the dosing frequency suitable for human is 1~12 times. Preferably, the dosing frequency for human is 1~6 times.

Preferably, the dosing frequency for human is 1~12 times every other day to every 30 days. Preferably, the dosing frequency for human is 1~6 times every other day to every 30 days. Or, preferably, the dosing frequency for human is 3~60 times every other day to every 20 days; preferably, the dosing frequency for human is 6~42 times every other day to every 14 days.

Experiment 7-5: The Effects of Administered Dosage on the Subcutaneous Fat of Rats In this experiment, rats were administered with different dosages of the curcumin-resveratrol complex pharmaceutical composition to assess the effects of administered dosage on the subcutaneous fat of rats. Additionally, in this experiment, other rats were administered with the main ingredient of another local lipolysis injection formulation currently undergoing clinical trials to simultaneously compare the effects of the curcumin-resveratrol complex pharmaceutical composition of the present invention and the other local lipolysis injection formulation currently undergoing clinical trials on the subcutaneous fat of rats.

A ELP solution, a LIPO-202 solution, and the curcumin-resveratrol complex pharmaceutical composition were prepared as follows:

The ELP solution: 18 g of KOLLIPHOR® ELP (also known as CREMOPHOR® ELP, polyoxyl 35 castor oil, abbreviated as ELP) was mixed with an appropriate amount of normal saline for injection to a total volume of 90 mL. The solution was mixed well to obtain the ELP solution. Wherein, the concentration of ELP was approximately 20%.

Preparation of the LIPO-202 Solution:

LIPO-202 is a local lipolysis injection formulation currently undergoing clinical trials, and its main ingredient is salmeterol xinafonate.
  (i) 1 mg of salmeterol xinafonate (purchased from Sigma-Aldrich) was mixed with an appropriate amount of methanol to a total volume of 1 mL to obtain a 1 mg/mL stock solution.
  (ii) The stock solution was 10-fold serial diluted with sterile water to prepare a salmeterol xinafonate solution of a final concentration of 0.01 µg/mL, which is the LIPO-202 solution used in this experiment.

Preparation of the Curcumin-Resveratrol Complex Pharmaceutical Composition:

same as the preparation of the curcumin-resveratrol complex solution comprising ELP described in Experiment 7-2. Wherein, the total concentration of curcumin and resveratrol was 5 mg/mL, and the ratio of curcumin to resveratrol was 4:1, and the concentration of ELP was 20%.

The rats were randomly assigned into 7 groups, which were a high-fat diet control group, a control group, a LIPO-202 group, a 1 mg/mL complex formula group, a 5 mg/mL complex formula group, a 10 mg/mL complex formula group, and a 20 mg/mL complex formula group. The rats were fed in the same manner described in Experiment 2.

The drugs were administered as follows:

The control group: The ELP solution was injected to the lower inguinal subcutaneous fat layer of rats in the control group. Each injection volume was 4 mL per kilogram of body weight (4 mL/kg).

The LIPO-202 group: The LIPO-202 solution was injected to the lower inguinal subcutaneous fat layer of rats in the LIPO-202 group. Each injection volume was 4 mL per kilogram of body weight (4 mL/kg), such that each injected dosage was 0.04 µg/kg (0.04 µg/kg; calculation: 0.01 µg/mL×4 mL/kg=0.04 µg/kg).

The 1 mg/mL complex formula group: The curcumin-resveratrol complex pharmaceutical composition was injected to the lower inguinal subcutaneous fat layer of rats in the 1 mg/mL complex formula group. Each injection volume was 0.2 mL per kilogram of body weight (0.2 mL/kg), such that each injected dosage was 1 mg/kg (1 mg/kg; calculation: 5 mg/mL×0.2 mL/kg=1 mg/kg).

The 5 mg/mL complex formula group: The curcumin-resveratrol complex pharmaceutical composition was injected to the lower inguinal subcutaneous fat layer of rats in the 5 mg/mL complex formula group. Each injection volume was 1 mL per kilogram of body weight (1 mL/kg), such that each injected dosage was 5 mg/kg (5 mg/kg; calculation: 5 mg/mL×1 mL/kg=5 mg/kg).

The 10 mg/mL complex formula group: The curcumin-resveratrol complex pharmaceutical composition was injected to the lower inguinal subcutaneous fat layer of rats in the 10 mg/mL complex formula group. Each injection volume was 2 mL per kilogram of body weight (2 mL/kg), such that each injected dosage was 10 mg/kg (10 mg/kg; calculation: 5 mg/mL×2 mL/kg=10 mg/kg).

The 20 mg/mL complex formula group: The curcumin-resveratrol complex pharmaceutical composition was injected to the lower inguinal subcutaneous fat layer of rats in the 20 mg/mL complex formula group. Each injection volume was 4 mL per kilogram of body weight (4 mL/kg), such that each injected dosage was 20 mg/kg (20 mg/kg; calculation: 5 mg/mL×4 mL/kg=20 mg/kg).

The high-fat diet control group: rats were injected with water for injection in the same manner described above.

Rats were injected once a day on day 1, 2, 3, and 4 of the experiment. The rats were fed with high-fat diet for the entire duration of the experiment. The experiment lasted for 14 days, and the rats were euthanized on day 15 by $CO_2$.

Figure 9:
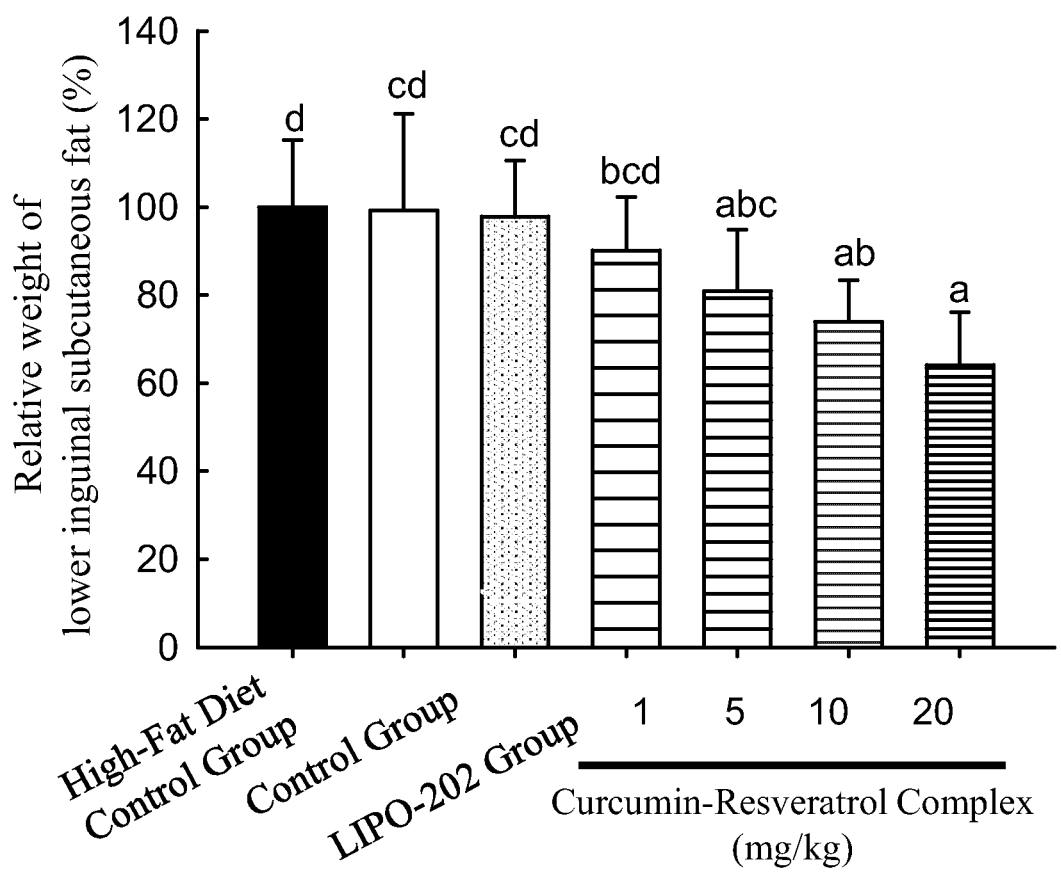
FIG. 9: A bar graph showing the effects of administered dosage of curcumin-resveratrol complex pharmaceutical composition on the amount of localized subcutaneous fat of rats.

Please refer to FIG. 9. FIG. 9 is a bar graph showing the effects of administered dosage of the curcumin-resveratrol complex pharmaceutical composition on localized subcutaneous fat of rats.

Results in FIG. 9 showed that the relative weight of the lower inguinal subcutaneous fat of rats in the high-fat diet control group was 100±15.2%, the relative weight of the lower inguinal subcutaneous fat of rats in the control group was 99.2±22.0%, the relative weight of the lower inguinal subcutaneous fat of rats in the LIPO-202 group was 97.8±12.8%, the relative weight of the lower inguinal subcutaneous fat of rats in the 1 mg/mL complex formula group was 90.1±12.2%, the relative weight of the lower inguinal subcutaneous fat of rats in the 5 mg/mL complex formula group was 80.9±13.9%, the relative weight of the lower inguinal subcutaneous fat of rats in the 10 mg/mL complex formula group was 73.9±9.5%, and the relative weight of the lower inguinal subcutaneous fat of rats in the 20 mg/mL complex formula group was 64.1±12.0%.

Therefore, the curcumin-resveratrol complex pharmaceutical composition achieved a significant local lipolysis effect at a dosage of 5 mg/kg, and the effects were more significant depend on the higher dosage. Although the dosage of 1 mg/kg of curcumin-resveratrol complex pharmaceutical composition did not achieve significant local lipolysis effect, but it induced a trend. Based on the experiences of the inventor, if dosing frequency is increased, the curcumin-resveratrol complex pharmaceutical composition can also achieve significant local lipolysis effect at a dosage of 1 mg/kg.

Based on the experiences of the inventor, when the administered dosage suitable for rats is 1 mg/kg~20 mg/kg, the administered dosage suitable for human is 0.01~40 mg/kg. Preferably, the administered dosage suitable for human is 0.1~20 mg/kg.

Preferably, the administered dosage suitable for human is 0.02~20 mg/cm². Preferably, the administered dosage suitable for human is 0.04~16 mg/cm². Preferably, the administered dosage suitable for human is 0.2~12 mg/cm². Preferably, the administered dosage suitable for human is 0.4~8 mg/cm².

Preferably, the administered dosage suitable for human is 0.01~40 mg/kg of body weight. Preferably, the administered dosage suitable for human is 0.4~40 mg/kg of body weight. Preferably, the administered dosage suitable for human is 0.8~20 mg/kg of body weight.

Experiment 8: The Effects of Curcumin Complex Pharmaceutical Compositions on Lipolysis This experiment used curcumin and lipophilic drugs other than resveratrol to prepare complex pharmaceutical compositions to assess the lipolysis efficacy of various lipophilic complex pharmaceutical compositions on mature adipocytes.

This experiment chose to use puerarin, quercetin, and synephrine to prepare various lipophilic complex pharmaceutical compositions.

Experiment 8-1 Cytotoxicity Test

Determine if 50 ppm of curcumin, puerarin, quercetin, or synephrine have toxicity to cells other than adipocytes by MTT assay. Only if the drug is deemed non-toxic will lipolysis test be proceeded.

Experimental results showed that 50 ppm of curcumin, puerarin, quercetin, and synephrine are not cytotoxic to rat somatic cells other than adipocytes, so this dosage will not affect the general somatic cells.

Experiment 8-2 Lipolysis Efficacy on Mature Adipocytes

A DMSO control group cell culture medium, a curcumin cell culture medium, a puerarin cell culture medium, a quercetin cell culture medium, a synephrine cell culture medium, a curcumin-puerarin complex cell culture medium, a curcumin-quercetin complex cell culture medium, and a curcumin-synephrine complex cell culture medium were prepared as follows:

The DMSO control group cell culture medium: DMSO was mixed with an appropriate amount of sterile water to obtain a 0.5% DMSO solution. The 0.5% DMSO solution was mixed with a cell culture medium (product name: Dulbecco's Modified Eagle Medium, purchased from Gibco) to prepare the DMSO control group cell culture medium, wherein, the volume ratio between the 0.5% DMSO solution and the cell culture medium was 1:1000.

The curcumin cell culture medium: curcumin was mixed with an appropriate amount of 0.5% DMSO solution to obtain a curcumin solution. The curcumin solution was mixed with a cell culture medium (product name: Dulbecco's Modified Eagle Medium, purchased from Gibco) to prepare the curcumin cell culture medium containing 50 ppm of curcumin, wherein, the volume ratio between the curcumin solution and the cell culture medium was 1:1000.

The puerarin cell culture medium: puerarin (purchased from Sigma-Aldrich) was mixed with an appropriate amount of 0.5% DMSO solution to obtain a puerarin solution. The puerarin solution was mixed with a cell culture medium to prepare the puerarin cell culture medium containing 50 ppm of puerarin, wherein, the volume ratio between the puerarin solution and the cell culture medium is 1:1000.

The quercetin cell culture medium: quercetin (purchased from Sigma-Aldrich) was mixed with an appropriate amount of 0.5% DMSO solution to obtain a quercetin solution. The quercetin solution was mixed with a cell culture medium to prepare the quercetin cell culture medium containing 50 ppm of quercetin, wherein, the volume ratio between the quercetin solution and the cell culture medium was 1:1000.

The synephrine cell culture medium: synephrine (purchased from Sigma-Aldrich) was mixed with an appropriate amount of 0.5% DMSO solution to obtain a synephrine solution. The synephrine solution was mixed with a cell culture medium to prepare the synephrine cell culture medium containing 50 ppm of synephrine, wherein, the volume ratio between the synephrine solution and the cell culture medium was 1:1000.

The curcumin-puerarin complex cell culture medium: curcumin and puerarin were mixed with an appropriate amount of 0.5% DMSO solution to obtain a curcumin-puerarin complex solution. Wherein, the weight ratio between curcumin and puerarin was 2:3. The curcumin-puerarin complex solution was mixed with a cell culture medium to prepare the curcumin-puerarin complex cell culture medium containing 50 ppm of curcumin-puerarin complex drug, wherein, the concentration of curcumin was 20 ppm, the concentration of puerarin was 30 ppm, and the volume ratio between the curcumin-puerarin complex solution and the cell culture medium was 1:1000.

The curcumin-quercetin complex cell culture medium: curcumin and quercetin were mixed with an appropriate amount of 0.5% DMSO solution to obtain a curcumin-quercetin complex solution. Wherein, the weight ratio between curcumin and quercetin was 2:3. The curcumin-quercetin complex solution was mixed with a cell culture medium to prepare the curcumin-quercetin complex cell culture medium containing 50 ppm of curcumin-quercetin complex drug, wherein, the concentration of curcumin was 20 ppm, the concentration of quercetin was 30 ppm, and the volume ratio between the curcumin-quercetin complex solution and the cell culture medium was 1:1000.

The curcumin-synephrine complex cell culture medium: curcumin and synephrine were mixed with an appropriate amount of 0.5% DMSO solution to obtain a curcumin-synephrine complex solution. Wherein, the weight ratio between curcumin and synephrine was 2:3. The curcumin-synephrine complex solution was mixed with a cell culture medium to prepare the curcumin-synephrine complex cell culture medium containing 50 ppm of curcumin-synephrine complex drug, wherein, the concentration of curcumin was 20 ppm, the concentration of synephrine was 30 ppm, and the volume ratio between the curcumin-synephrine complex solution and the cell culture medium was 1:1000.

Experimental procedure to determine the lipolysis efficacy on mature adipocytes The adipocyte precursors 3T3-L1 cells (purchased from the Food Industry Research and Development Institute, Taiwan; abbreviated as BCRC) were seeded in 12-well plates, such that each well contained $1\times10^5$ cells. After two days of culture, the cells were cultured for another two days in a cell differentiation induction media (DMI medium, wherein contains 0.5 μM of IBMX (purchased from Sigma-Aldrich), 0.1 μM of dexamethasone (purchased from Sigma-Aldrich), and 5 μg/ml of insulin (purchased from Humulin R.)) Then, the cells were cultured in a medium containing 5 μg/ml of insulin. Once the cell morphology changed from spindle-shaped to spherical and many lipid droplets were accumulated in the cells, it indicated that the cells have differentiated into mature adipocytes.

The mature adipocytes were assigned into 8 groups, which were a DMSO control group, a curcumin group, a puerarin group, a quercetin group, a synephrine group, a curcumin-puerarin complex group, a curcumin-quercetin complex group, and a curcumin-synephrine complex group.

The mature adipocytes in the DMSO control group, the curcumin group, the puerann group, the quercetin group, the synephrine group, the curcumin-puerarin complex group, the curcumin-quercetin complex group, and the curcumin-synephrine complex group were respectively cultured with the DMSO control group cell culture medium, the curcumin cell culture medium, the puerarin cell culture medium, the quercetin cell culture medium, the synephrine cell culture medium, the curcumin-puerarin complex cell culture medium, the curcumin-quercetin complex cell culture medium, and the curcumin-synephrine complex cell culture medium for 24 hours.

Annexin V protein (purchased from eBioscience) and propidium iodide (PI; purchased from eBioscience) were mixed with the cells in each group for a period of time, and then the percentage of cells labeled by annexin V protein and PI in each group was analyzed by flow cytometry to assess the percentage of mature adipocytes undergoing apoptosis. Wherein, when a mature adipocyte is labeled by both annexin V protein and PI, it indicates that the cell is undergoing apoptosis; when more mature adipocytes are undergoing apoptosis, it indicates that the lipolysis efficacy of the administered drug is better, and it also indicates that lipolysis is mediated through apoptosis but not necrosis.

The data were presented as mean±SD and analyzed by one-way ANOVA. Statistical results were shown as symbols or letters. Different symbols or letters indicates statistically significant difference ($p<0.05$), and identical symbols or letters indicates no statistically significant difference ($p>0.05$).

Because the total dosage of the administered drug in each group was 50 ppm, the apoptosis efficacy of the curcumin-puerarin complex group should be between the efficacy of the curcumin group and the puerarin group. If the apoptosis efficacy of the curcumin-puerarin complex group is better than that of the curcumin group and the puerarin group, it indicates that curcumin and puerarin in the curcumin-puerarin complex group manifests synergy in lipolysis efficacy. Similarly, the apoptosis efficacy of the curcumin-quercetin complex group should be between the efficacy of the curcumin group and the quercetin group. If the apoptosis efficacy of the curcumin-quercetin complex group is better than that of the curcumin group and the quercetin group, it indicates that curcumin and quercetin in the curcumin-quercetin complex group manifests synergy in lipolysis efficacy. The apoptosis efficacy of the curcumin-synephrine complex group should be between the efficacy of the curcumin group and the synephrine group. If the apoptosis efficacy of the curcumin-synephrine complex group is better than that of the curcumin group and the synephrine group, it indicates that curcumin and synephrine in the curcumin-synephrine complex group manifests synergy in lipolysis efficacy.

Figure 10:
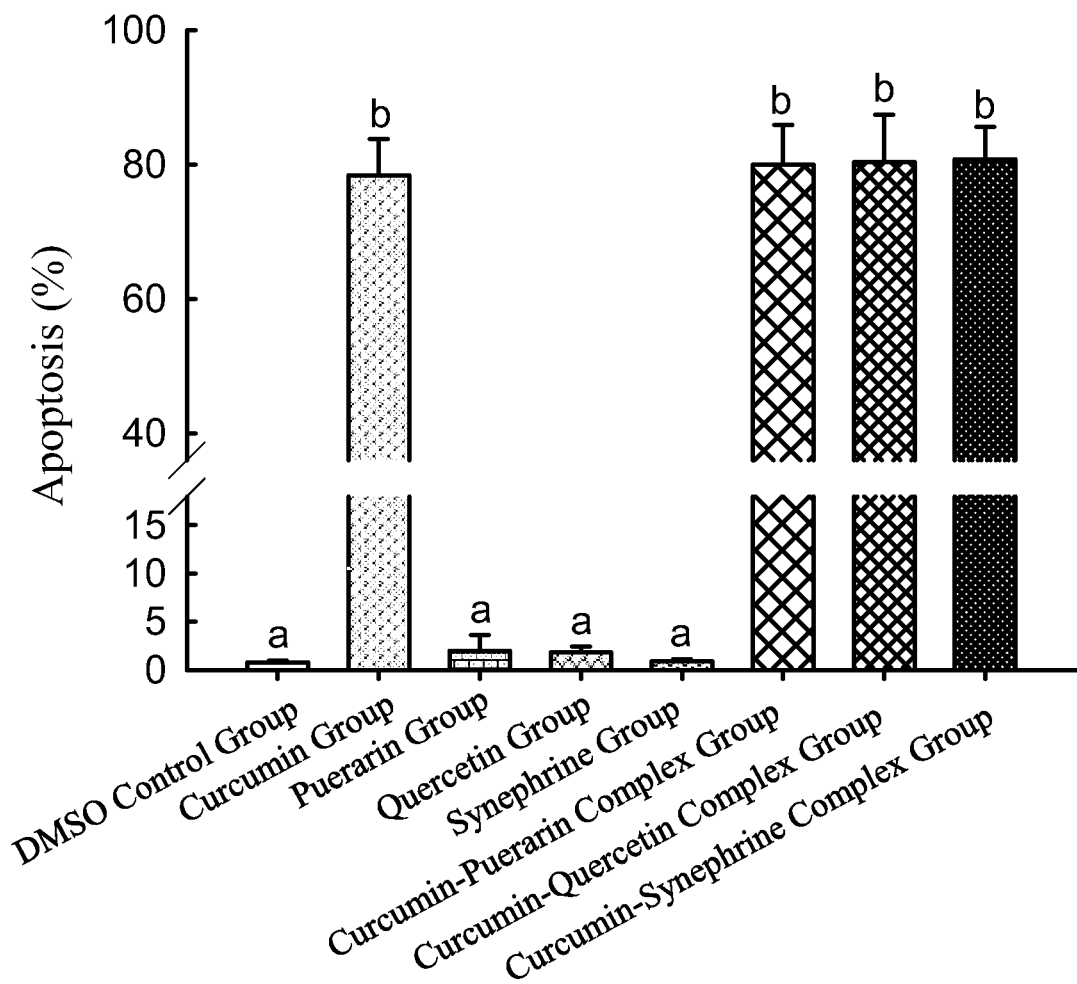
FIG. 10: The effects of curcumin-other lipophilic drug complex pharmaceutical compositions on the apoptosis of mature adipocytes.

Please refer to FIG. 10. FIG. 10 is a bar graph showing the effects of curcumin-other lipophilic drug complex pharmaceutical compositions on promoting apoptosis of mature adipocytes Results in FIG. 10 showed that the percentage of apoptotic cells of the DMSO control group was 0.8±0.2%, the percentage of apoptotic cells of the curcumin group was 78.4±5.4%, the percentage of apoptotic cells of the puerarin group was 2.0±1.6%, the percentage of apoptotic cells of the quercetin group was 1.8±0.6%, the percentage of apoptotic cells in the synephrine group was 0.9±0.2%, the percentage of apoptotic cells of the curcumin-puerarin complex group was 80.0±5.9%, the percentage of apoptotic cells of the curcumin-quercetin complex group was 80.4±7.0%, and the percentage of apoptotic cells of the curcumin-synephrine complex group was 80.8±4.8%.

Comparison among the apoptosis efficacy of the curcumin group, the puerarin group, and the curcumin-puerarin complex group demonstrated that curcumin and puerarin in the curcumin-puerarin complex pharmaceutical composition manifests synergy in lipolysis efficacy.

Comparison among the apoptosis efficacy of the curcumin group, the quercetin group, and the curcumin-quercetin complex group demonstrated that curcumin and quercetin in the curcumin-quercetin complex pharmaceutical composition manifests synergy in lipolysis efficacy.

Comparison among the apoptosis efficacy of the curcumin group, the synephrine group, and the curcumin-synephrine complex group demonstrated that curcumin and synephrine in the curcumin-quercetin complex pharmaceutical composition manifests synergy in lipolysis efficacy.

Therefore, complex pharmaceutical compositions formed by curcumin and various lipophilic drugs can all achieve the effect of lipolysis, and there are synergies between curcumin and various lipophilic drugs in the lipolysis efficacy. Therefore, the present invention uses curcumin and various lipophilic drugs to prepare drug-containing micelles and a second lipophilic drug-containing micelles, and further prepares the curcumin-other lipophilic drug complex pharmaceutical compositions, which are the pharmaceutical compositions capable of being used for localized lipolysis and weight reduction.

The present invention provides a first preparation method for preparing a curcumin-other lipophilic drug complex pharmaceutical composition, and the curcumin-other lipophilic drug complex pharmaceutical composition comprises drug-containing micelles and the second lipophilic drug-containing micelles; the procedure of the first preparation to prepare the curcumin-other lipophilic drug complex pharmaceutical composition is as follows:
- (A) Steps to prepare drug-containing micellar subassembly, to prepare a drug-containing micellar subassembly;
- (B) Steps to prepare a second lipophilic drug-containing micellar subassembly, to prepare the second lipophilic drug-containing micellar subassembly; and
- (C) Mixing the drug-containing micellar subassembly with the second lipophilic drug-containing micellar subassembly, to prepare the curcumin-other lipophilic drug complex pharmaceutical composition;

Wherein, the step (A) to prepare the drug-containing micellar subassembly comprises the following steps (a2)~(d2)
- (a2) Mixing curcumin with a first solvent, and stirring at 150~500 rpm at room temperature until curcumin dissolves completely;
- (b2) Adding a first pharmaceutically acceptable surfactant, and stirring well at 100~300 rpm to volatilize the first solvent, wherein the hydrophilic-lipophilic balance value (HLB value) of the first surfactant is greater than 10;
- (c2) After the first solvent volatilizes completely, obtaining the drug-containing micelles; and
- (d2) Filtering through a 0.2 um filter, and the filtered solution is the drug-containing micellar subassembly comprising drug-containing micelles;

Moreover, the step (B) to prepare the second lipophilic drug-containing micellar subassembly comprises the following steps (a3)~(d3):
- (a3) Mixing a second lipophilic drug with a second solvent, and stirring at 200~500 rpm at room temperature until the second lipophilic drug dissolves completely;
- (b3) Adding a second pharmaceutically acceptable surfactant, and stirring well at 100~300 rpm to volatilize the second solvent, wherein the hydrophilic-lipophilic balance value (HLB value) of the second surfactant is greater than 10;
- (c3) After the second solvent volatilizes completely, obtaining the second lipophilic drug-containing micelles; and
- (d3) Filtering through a 0.2 um filter, and the filtered solution is the second lipophilic drug-containing micellar subassembly comprising the second lipophilic drug-containing micelles.

Wherein, in step (c2), the drug-containing micelle is a microstructure formed by a surfactant, and curcumin is encapsulated in said drug-containing micelle. In step (c3), the second lipophilic drug-containing micelle is a microstructure formed by the second surfactant, and the second lipophilic drug is encapsulated in said second lipophilic drug-containing micelle.

Preferably, the operating procedure of step (c2) is: After the first solvent volatilizes completely, slowly adding a pharmaceutically acceptable aqueous solution and mixing well to form drug-containing micelles.

Preferably, the operating procedure of step (c3) is: After the second solvent volatilizes completely, slowly adding a pharmaceutically acceptable aqueous solution and mixing well to form the second lipophilic drug-containing micelles.

Preferably, the second lipophilic drug is at least one of quercetin, synephrine, puerarin, resveratrol, and any lipophilic drug except curcumin, or combination thereof.

Preferably, in step (a2) and/or step (a3), the boiling point(s) of the first solvent and/or the second solvent are/is lower than the boiling point of pure water.

Preferably, in step (a2) and/or step (a3), the first solvent and/or the second solvent are/is a hydrophilic solvent.

Preferably, the hydrophilic solvent is at least one of methanol, ethanol, acetone, and other hydrophilic solvents, or combination thereof.

Preferably, in step (a2) and/or step (a3), the first solvent and/or the second solvent are/is a lipophilic solvent.

Preferably, the lipophilic (hydrophobic) solvent is at least one of ether, benzene, chloroform, dichloromethane, hexane, and other lipophilic (hydrophobic) solvents, or combination thereof.

Preferably, in step (b2) and/or (b3), the first surfactant and/or the second surfactant are/is a non-ionic surfactant.

Preferably, the non-ionic surfactant is at least one of polysorbate 80 (TWEEN® 80), polyoxyl 15 hydroxystearate (SOLUTOL® HS 15), polyoxyethylene castor oil derivatives, and other non-ionic surfactants, or combination thereof.

Preferably, the polyoxyethylene castor oil derivative is at least one of KOLLIPHOR® ELP (also known as CREMOPHOR® ELP, polyoxyl 35 castor oil), CREMOPHOR® RH 40 (polyoxyl 40 hydrogenated castor oil), and other polyoxyethylene castor oil derivatives, or combination thereof.

Preferably, the weight ratio of curcumin to the second lipophilic drug is 30:1~1:10.

Preferably, in steps (a2) and (b2), the weight ratio of the curcumin and the first surfactant is 1:4 to 1:500.

Preferably, in steps (a3) and (b3), the weight ratio of the second lipophilic drug and the second surfactant is 1:4 to 1:500.

Preferably, in step (c2) and/or (c3), the pharmaceutically acceptable aqueous solution is water for injection, aqueous solution for injection, or normal saline.

Preferably, in step (c2) and/or (c3), the pharmaceutically acceptable aqueous solution comprises a local anesthetic.

Preferably, the local anesthetic is at least one of amides, para-aminobenzoic acid esters, and amino ethers, or combination thereof Preferably, the amides are at least one of dibucaine, lidocaine, mepivacaine HCl, bupivacine HCl, pyrrocaine HCl, Prilocaine HCl, digammacaine, and oxethazaine, or combination thereof.

Preferably, the para-aminobenzoic acid esters are at least one of butacaine, dimethocaine, and tutocaine, or combination thereof.

Preferably, the amino ethers are at least one of quinisocaine and pramocaine, or combination thereof.

Preferably, in step (c2) and/or (c3), the pharmaceutically acceptable aqueous solution comprises an antioxidant.

Preferably, the antioxidant is at least one of beta-carotene, lutein, lycopene, bilirubin, vitamin A, vitamin C (ascorbic acid), vitamin E, uric acid, nitric oxide, nitroxide, pyruvate, catalase, superoxide dismutase, glutathione peroxidases, N-acetyl cysteine, and naringenin, or combination thereof.

The present invention provides a second preparation of the curcumin-other lipophilic drug complex pharmaceutical composition, and the second preparation method of the curcumin-other lipophilic drug complex pharmaceutical composition is more concise than the first preparation method of the curcumin-other lipophilic drug complex pharmaceutical composition; the procedure of the second preparation method for the curcumin-other lipophilic drug complex pharmaceutical composition is as follows:

(a4) Mixing curcumin, the second lipophilic drug, and a solvent, and stirring at 200~500 rpm until curcumin dissolves completely;

(b4) Adding a pharmaceutically acceptable surfactant and stirring well at 100~300 rpm to volatilize the solvent, wherein, the hydrophilic-lipophilic balance value (HLB value) of the surfactant is greater than 10;

(c4) Once the solvent volatilizes completely, slowly adding a pharmaceutically acceptable aqueous solution and mixing well to form drug-containing micelles and the second lipophilic drug-containing micelles; and (d4) Filtering through a 0.2 um filter, and storing the filtered solution comprising the drug-containing micelles and the second lipophilic drug-containing micelles in dark and refrigeration.

The types and ranges of the solvents, the surfactants, the pharmaceutically acceptable aqueous solutions, and the second lipophilic drugs used in the second preparation for the curcumin-other lipophilic drug complex pharmaceutical composition are the same as those used in the first preparation of the curcumin-other lipophilic drug complex pharmaceutical composition. Additionally, the ranges of relative ratios of the ingredients used in the second preparation of the curcumin-other lipophilic drug complex pharmaceutical composition are the same as those of the first preparation of the curcumin-other lipophilic drug complex pharmaceutical composition.

Preferably, the pharmaceutical composition comprises a local aesthetic and/or an antioxidant.

Preferably, the types and ranges of the local anesthetics and the antioxidants of the second preparation of the curcumin-other lipophilic drug complex pharmaceutical composition are the same as those used in the first preparation of the curcumin-other lipophilic drug complex pharmaceutical composition.

Experiment 9: The Effects of Curcumin-Green Tea Extract Complex Subcutaneous Injection Formulation on the Subcutaneous Fat of Rats Experiment 9-1: The Effects of Green Tea Extract Simple Subcutaneous Injection Formulation on the Subcutaneous Fat of Rats Preparation of the Green Tea Extract Subcutaneous Injection Formulation:

Green tea extract was mixed with an appropriate amount of normal saline for injection to obtain the green tea extract subcutaneous injection formulation.

The rats were assigned into a high-fat diet control group and a green tea extract group with 6 rats in each group. The rats were fed in the same manner described in Experiment 2. The green tea extract subcutaneous injection formulation was injected into the lower inguinal subcutaneous fat layer of rats in the green tea extract group. Each injected dosage was 8 mg of green tea extract per kilogram of body weight (8 mg/kg). Rats in the high-fat diet control group were injected with the same volume of water for injection in the same manner described above.

The injection sites mentioned above were the lower inguinal fat pads of rats. Bilateral injections were administered evenly once a day on day 1, 3, and 5 of the experiment. The rats were fed with high-fat diet for the entire duration of the experiment. Their weight changes were recorded daily, and food and water consumption was recorded weekly. The experiment lasted for 20 days, and the rats were euthanized on day 21 by $CO_2$.

Figure 11:
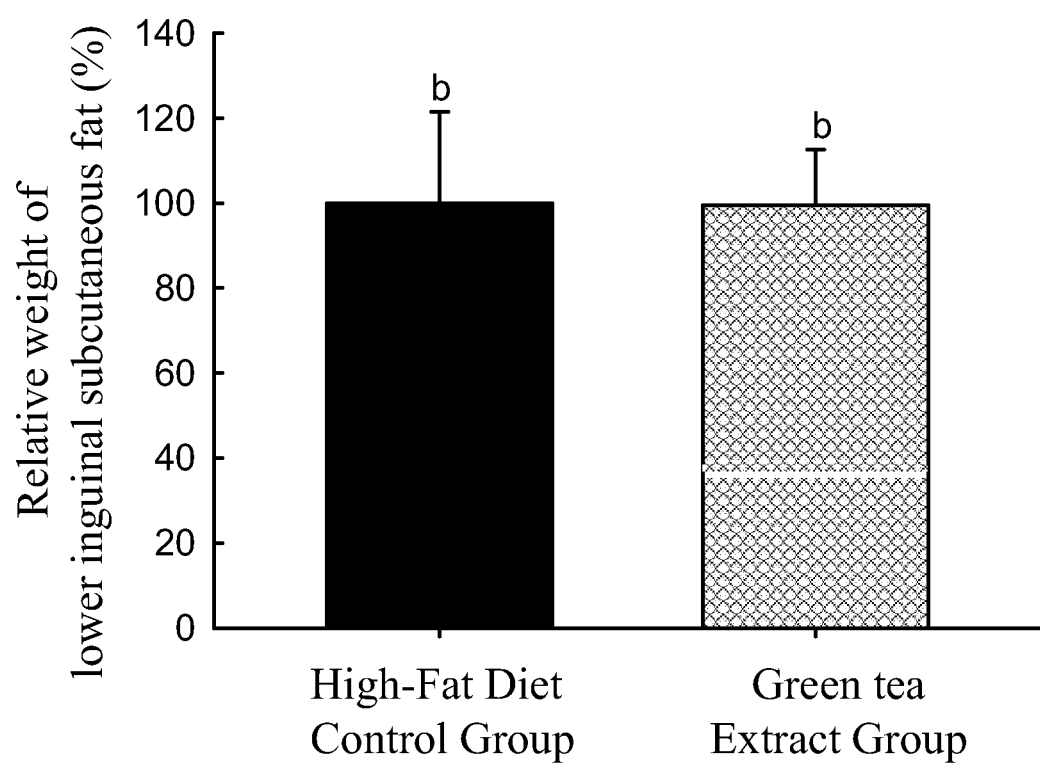
FIG. 11: A bar graph showing the effects of green tea extract subcutaneous injection formulation without excipient on the amount of localized subcutaneous fat of rats.

Please refer to FIG. 11. FIG. 11 is a bar graph showing the effects of the green tea extract subcutaneous injection formulation without excipient on localized subcutaneous fat of rats Results in FIG. 11 showed that the relative weight of the lower inguinal subcutaneous fat of rats in the high-fat diet control group was 100.00±21.51%, the relative weight of the lower inguinal subcutaneous fat of rats in the green tea extract group was 99.50±13.14%. There was no significant difference between the relative weight of the lower inguinal subcutaneous fat of rats in the green tea extract group and that of rats in the high-fat diet control group, indicating that a hydrophilic plant extract-green tea extract composition without excipient cannot reduce the fat at the administration site (localized fat).

Experiment 9-2: The Effects of Dosing Frequency on the Subcutaneous Fat and the Body Weight of Rats In this experiment, rats in each group were administered with an equal amount of total injected dosage of the curcumin-green tea extract complex pharmaceutical composition but with different dosing frequency to assess the effects of dosing frequency on the subcutaneous fat and the body weight of rats. In this experiment, other rats were administered with the main ingredient of a local lipolysis injection formulation available in the market to simultaneously compare the effects of the curcumin-green tea extract complex pharmaceutical composition of the present invention and the local lipolysis injection formulation in the market on the subcutaneous fat and the body weight of rats.

A sodium deoxycholate solution and the curcumin-green tea extract complex pharmaceutical composition were prepared as follows:

Preparation of the sodium deoxycholate solution: same as the preparation of the sodium deoxycholate solution in Experiment 7-4.

Preparation of the curcumin-green tea extract complex pharmaceutical composition: 0.8 g of curcumin was mixed with 150~200 mL of dichloromethane and stirred at 150~500 rpm to completely dissolve curcumin. 40 g of KOLLIPHOR® ELP (also known as CREMOPHOR® ELP, polyoxyl 35 castor oil, abbreviated as ELP) was added and stirred at 100~300 rpm to volatilize dichloromethane. Once dichloromethane volatilized completely, normal saline for injection was slowly added to a total volume of 200 mL. Wherein, the normal saline for injection comprised 0.2 g of green tea extract. The solution was mixed well to obtain the curcumin-green tea extract complex solution comprising ELP. Said curcumin-green tea extract complex solution comprising ELP comprised drug-containing micelles, the total concentration of curcumin and green tea was 5 mg/mL, and the weight ratio of curcumin and green tea extract was 4:1

The rats were randomly assigned into 4 groups, which were a high-fat diet control group, a sodium deoxycholate group, a high-dosing frequency curcumin-green tea extract group (abbreviated as high-dosing frequency group in this experiment), and a low-dosing frequency curcumin-green tea extract group (abbreviated as low-dosing frequency group). The rats were fed in the same manner described in Experiment 2.

The drugs were administered as follows:

The sodium deoxycholate group: The sodium deoxycholate solution was injected to the lower inguinal subcutaneous fat layer of rats in the sodium deoxycholate group. Each injection volume was 4 mL per kilogram of body weight (4 mL/kg), such that each injected dosage was 10.3 mg/kg (10.3 mg/kg; calculation: 2.575 mg/mL×4 mL/kg=10.3 mg/kg). Rats were injected once a day on day 1, 3, and 5 of the experiment, with 3 injections in total, such that the total dosage was 30.9 mg/kg (10.3 mg/kg×3 times=30.9 mg/kg).

The high-dosing frequency group: The curcumin-green tea extract complex pharmaceutical composition was injected to the lower inguinal subcutaneous fat layer of rats in the high-dosing frequency group. Each injection volume was 4 mL per kilogram of body weight (4 mL/kg), such that each injected dosage was 20 mg/kg (20 mg/kg; calculation: 5 mg/mL×4 mL/kg=20 mg/kg). Rats were injected once a day on day 1, 3, 5, 7, 9, and 11 of the experiment, with 6 injections in total, such that the total dosage was 120 mg/kg (20 mg/kg×6 times=120 mg/kg).

The low-dosing frequency group: The curcumin-green tea extract complex pharmaceutical composition was injected to the lower inguinal subcutaneous fat layer of rats in the low-dosing frequency group. Each injection volume was 8 mL per kilogram of body weight (8 mL/kg), such that each injected dosage was 40 mg/kg (40 mg/kg; calculation: 5 mg/mL×8 mL/kg=40 mg/kg). Rats were injected once a day on day 1, 3, and 5 of the experiment, with 3 injections in total, such that the total dosage was 120 mg/kg (40 mg/kg×3 times=120 mg/kg).

The high-fat diet control group: rats were injected with water for injection in the same manner described above.

The rats were fed with high-fat diet for the entire duration of the experiment. The experiment lasted for 20 days, and the rats were euthanized on day 21 by $CO_2$.

Figure 12A:
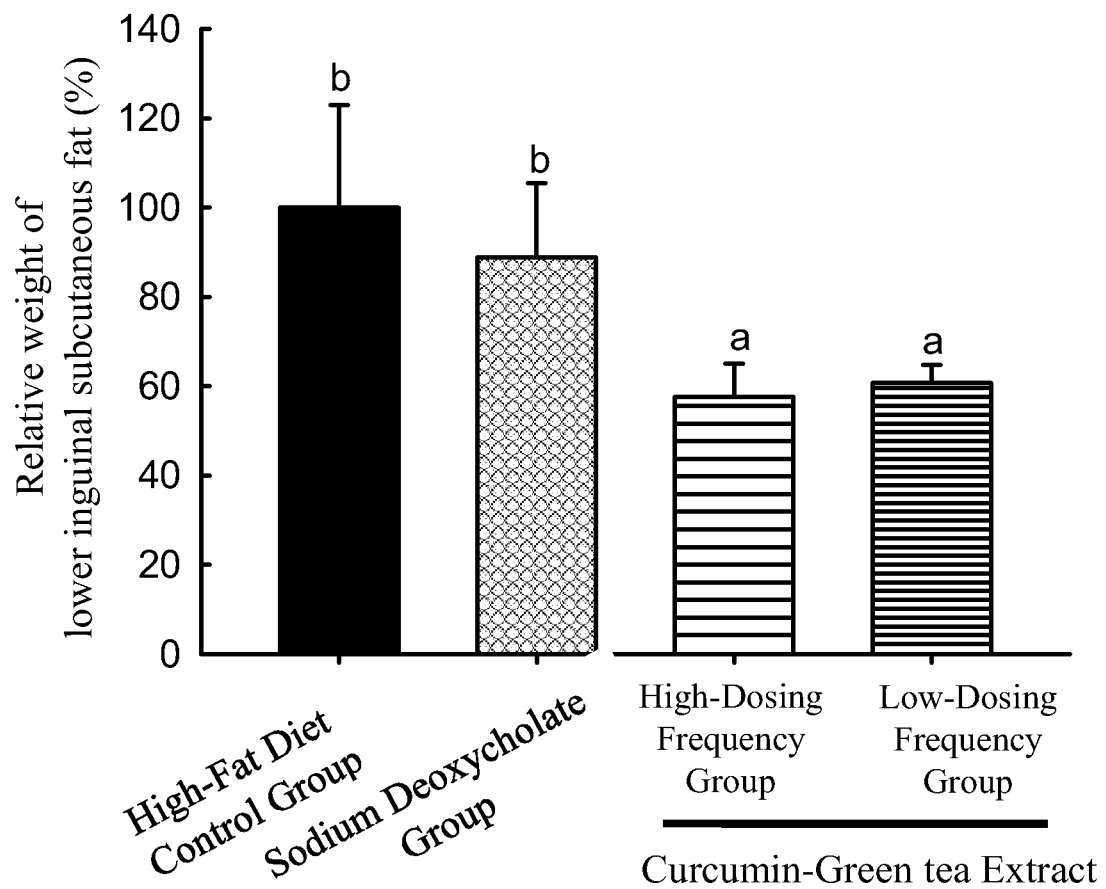
FIG. 12A: A bar graph showing the effects of dosing frequency of curcumin-green tea extract complex pharmaceutical composition on the amount of localized subcutaneous fat of rats.
Figure 12B:
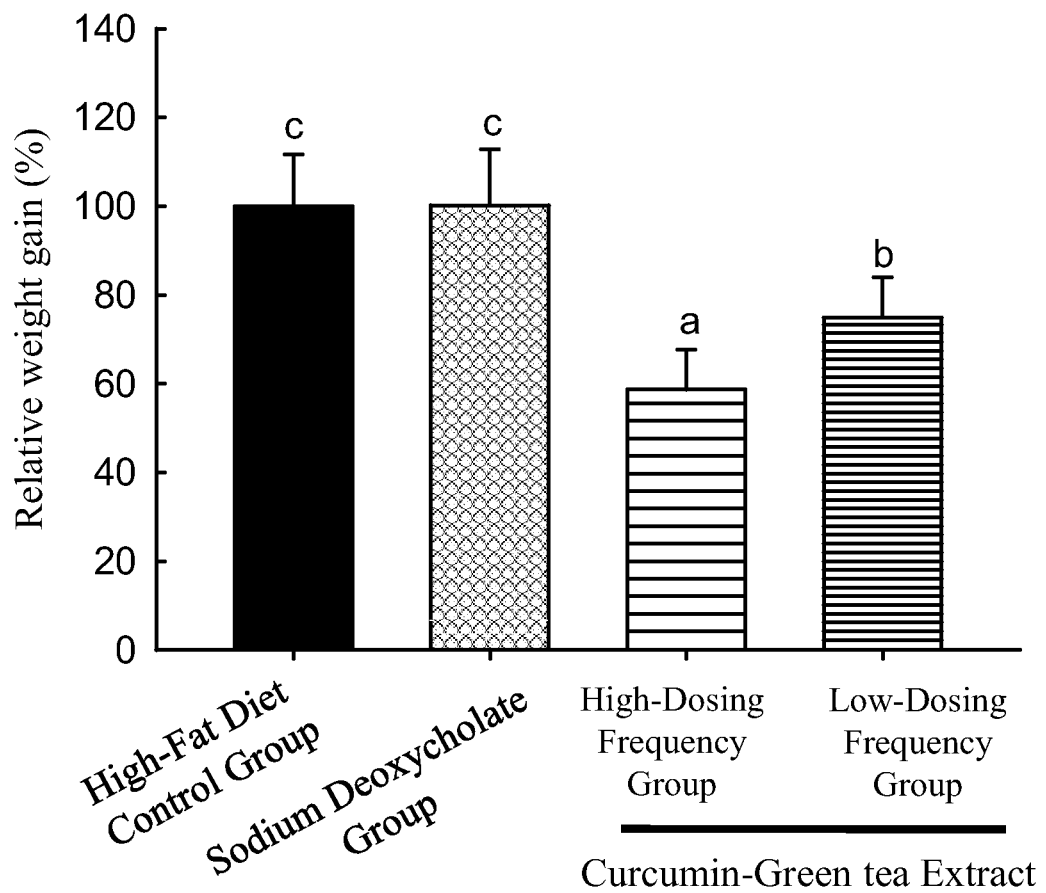
FIG. 12B: A bar graph showing the effects of dosing frequency of curcumin-green tea extract complex pharmaceutical composition on total body weight gain of rats.

Please refer to FIGS. 12A and 12B. FIG. 12A is a bar graph showing the effects of the dosing frequency of the curcumin-green tea extract complex pharmaceutical composition on localized subcutaneous fat of rats. FIG. 12B is a bar graph showing the effect of the dosing frequency of the curcumin-green tea extract complex pharmaceutical composition on total body weight gain of rats.

Results in FIG. 12A showed that the relative weight of the lower inguinal subcutaneous fat of rats in the high-fat diet control group was 100.0±22.6%, the relative weight of the lower inguinal subcutaneous fat of rats in the sodium deoxycholate group was 88.8±16.7%, the relative weight of the lower inguinal subcutaneous fat of rats in the high-dosing frequency group was 57.6±7.4%, and the relative weight of the lower inguinal subcutaneous fat of rats in the low-dosing frequency group was 60.7±4.0%.

Comparing to the high-fat diet control group, both the high-dosing frequency group and the low-dosing frequency group can significantly reduce the fat at the administration site (localized fat) ($p<0.05$). Thus, if the concentration of the curcumin-green tea extract complex pharmaceutical composition is sufficient, low-dosing frequency can achieve the effect of local lipolysis.

Comparing to the low-dosing frequency group, the lipolysis effect of the high-dosing frequency group is better. Although there was no significant difference between high-dosing frequency and low-dosing frequency, the high-dosing frequency can achieve a better trend of local lipolysis effect.

Results in FIG. 12B showed that the relative weight gain of rats in the high-fat diet control group was 100.0±11.6%, the relative weight gain of rats in the sodium deoxycholate group was 100.2±12.6%, the relative weight gain of rats in the high-dosing frequency group was 58.7±9.0%, and the relative weight gain of rats in the low-dosing frequency group was 74.9±9.0%. Comparing to the relative weight gain of rats in the high-fat diet control group, the relative weight gain of rats in both the low-dosing frequency group and the high-dosing frequency group was significantly decreased ($p<0.05$), and the relative weight gain was reduced by 25.1% and 41.3%, respectively, showing that the weight loss effect was very significant.

Therefore, the curcumin-green tea extract complex pharmaceutical composition of the present invention can significantly reduce the body weight, and the weight loss efficacy of high-dosing frequency is significantly better than that of low-dosing frequency ($p<0.05$).

Based on the experiences of the inventor, when the dosing frequency suitable for rats is 3~6 times, the dosing frequency suitable for human is 1~12 times. Preferably, the dosing frequency for human is 1~6 times.

Preferably, the dosing frequency for human is 1~12 times every other day to every 30 days. Preferably, the dosing frequency for human is 1~6 times every other day to every 30 days. Or, preferably, the dosing frequency for human is 3~60 times every other day to every 20 days; preferably, the dosing frequency for human is 6~42 times every other day to every 14 days.

Experiment 10: The Effects of Curcumin Complex Pharmaceutical Compositions on Lipolysis Curcumin and hydrophilic drugs expect green tea extract were used in this experiment to prepare complex pharmaceutical compositions to assess the lipolysis efficacy of various hydrophilic complex pharmaceutical compositions on mature adipocytes.

This experiment uses caffeine and L-carnitine to prepare various hydrophilic complex pharmaceutical compositions.

Experiment 10-1: Cytotoxicity Test

Determine if 50 ppm of caffeine and L-carnitine have toxicity to cells other than adipocytes by MTT assay. Only if the drug is deemed non-toxic will lipolysis test be proceeded.

Experimental results showed that 50 ppm of caffeine and L-carnitine are not cytotoxic to rat somatic cells expect adipocytes, so this dosage will not affect the general somatic cells.

Experiment 10-2: Lipolysis Efficacy on Mature Adipocytes

A sterile water control group cell culture medium, a curcumin cell culture medium, a caffeine cell culture medium, an L-carnitine cell culture medium, a curcumin-caffeine complex cell culture medium, and a curcumin-L-carnitine complex cell culture medium were prepared as follows:

The sterile water control group cell culture medium: Sterile water was mixed with a cell culture medium to prepare the sterile water control group cell culture medium. Wherein, the volume ratio of sterile water and the cell culture medium was 1:1000.

The curcumin cell culture medium: same as the preparation of the curcumin cell culture medium in Experiment 8-2.

The caffeine cell culture medium: Caffeine (purchased from Sigma-Aldrich) was mixed with an appropriate amount of sterile water to obtain a caffeine solution. The caffeine solution was mixed with a cell culture medium to prepare the caffeine cell culture medium containing 50 ppm of caffeine. Wherein, the volume ratio of the caffeine cell culture medium and the cell culture medium was 1:1000.

The L-carnitine cell culture medium: L-carnitine (purchased from Sigma-Aldrich) was mixed with an appropriate amount of sterile water to obtain a L-carnitine solution. The L-carnitine solution was mixed with a cell culture medium to prepare the caffeine cell culture medium containing 50 ppm of L-carnitine. Wherein, the volume ratio of the L-carnitine cell culture medium and the cell culture medium was 1:1000.

The curcumin-caffeine complex cell culture medium: Curcumin and caffeine were mixed with an appropriate amount of sterile water to prepare a curcumin-caffeine complex solution. Wherein, the weight ratio of curcumin and caffeine was 2:3. The curcumin-caffeine complex solution was mixed with a cell culture medium to prepare the curcumin-caffeine complex cell culture medium containing 50 ppm of curcumin-caffeine complex drug. Wherein, the concentration of curcumin was 20 ppm, the concentration of caffeine was 30 ppm, and the volume ratio of the curcumin-caffeine complex solution and the cell culture medium was 1:1000.

The curcumin-L-carnitine complex cell culture medium: Curcumin and L-carnitine were mixed with an appropriate amount of sterile water to prepare a curcumin-L-carnitine complex solution. Wherein, the weight ratio of curcumin and L-carnitine was 2:3. The curcumin-L-carnitine complex solution was mixed with a cell culture medium to prepare the curcumin-L-carnitine complex cell culture medium containing 50 ppm of curcumin-L-carnitine complex drug. Wherein, the concentration of curcumin was 20 ppm, the concentration of L-carnitine was 30 ppm, and the volume ratio of the curcumin-L-carnitine complex solution and the cell culture medium was 1:1000.

Preparation of the Mature Adipocytes was the Same as that of Experiment 8-2.

The adipocytes were assigned into 6 groups, which were a sterile water group, a curcumin group, a caffeine group, an L-carnitine group, a curcumin-caffeine complex group, and a curcumin-L-carnitine complex group.

The mature adipocytes in the sterile water group, the curcumin group, the caffeine group, the L-carnitine group, the curcumin-caffeine complex group, and the curcumin-L-carnitine complex group were cultured with the sterile water control group cell culture medium, the curcumin cell culture medium, the caffeine cell culture medium, the L-carnitine cell culture medium, the curcumin-caffeine complex cell culture medium, and the curcumin-L-carnitine complex cell culture medium, respectively, for 24 hours.

Annexin V protein (purchased from eBioscience) and propidium iodide (PI; purchased from eBioscience) were mixed with the cells in each group for a period of time, and then the percentage of cells labeled by annexin V protein and PI in each group was analyzed by flow cytometry to assess the percentage of mature adipocytes undergoing apoptosis. Wherein, when a mature adipocyte is labeled by both annexin V protein and Pl, it indicates that the cell is undergoing apoptosis; when more mature adipocytes are undergoing apoptosis, it indicates that the lipolysis efficacy of the administered drug is better, and it also indicates that lipolysis is mediated through apoptosis but not necrosis.

Because the total dosage of the administered drug was 50 ppm, and 40% was curcumin and 60% was caffeine, therefore, the lipolysis efficacy of the curcumin-caffeine complex group should be close to the average of that of the curcumin group and the caffeine group. If the lipolysis efficacy of the curcumin-caffeine complex group is significantly better than the average of the curcumin group and the caffeine group, it indicates that curcumin and caffeine in the curcumin-caffeine complex pharmaceutical composition manifests synergy. Similarly, because the total dosage of the administered drug was 50 ppm, and 40% was curcumin and 60% was L-carnitine, therefore, the lipolysis efficacy of the curcumin-L-carnitine complex group should be close to the average of that of the curcumin group and the caffeine group. If the lipolysis efficacy of the curcumin-L-carnitine complex group is significantly better than the average of the curcumin group and the L-carnitine group, it indicates that curcumin and L-carnitine in the curcumin-L-carnitine complex pharmaceutical composition manifests synergy.

Figure 13:
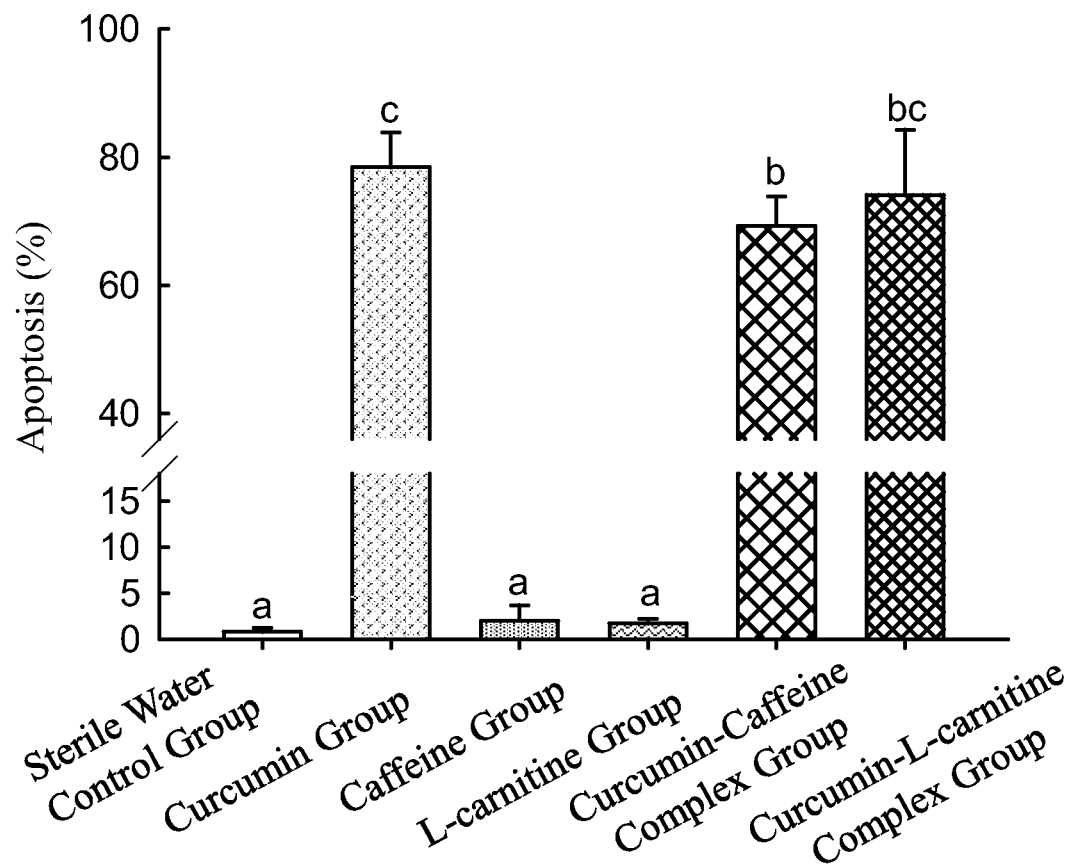
FIG. 13: The effects of curcumin-other hydrophilic drug complex pharmaceutical compositions on the apoptosis of mature adipocytes.

Please refer to FIG. 13. FIG. 13 is a bar graph showing the effects of curcumin-other hydrophilic drug complex pharmaceutical compositions on promoting apoptosis of mature adipocytes.

Results in FIG. 13 showed that the percentage of apoptotic cells of the sterile water control group was 0.8±0.4%, the percentage of apoptotic cells of the curcumin group was 78.4±5.4%, the percentage of apoptotic cells of the caffeine group was 2.0±1.7%, the percentage of apoptotic cells of the L-carnitine group was 1.7±0.5%, the percentage of apoptotic cells of the curcumin-caffeine complex group was 69.3±4.5%, and the percentage of apoptotic cells of the curcumin-L-carnitine complex group was 74.1±10.2%.

Comparison among the apoptosis efficacy of the curcumin group, the caffeine group, and the curcumin-caffeine complex group demonstrated that curcumin and caffeine in the curcumin-caffeine complex pharmaceutical composition manifests synergy in lipolysis efficacy.

Comparison among the apoptosis efficacy of the curcumin group, the L-carnitine group, and the curcumin-L-carnitine complex group demonstrated that curcumin and L-carnitine in the curcumin-L-carnitine complex pharmaceutical composition manifests synergy in lipolysis efficacy.

Therefore, complex pharmaceutical compositions formed by curcumin and various hydrophilic drugs can all achieve the effect of lipolysis, and there are synergies between curcumin and various hydrophilic drugs in the effects of lipolysis. Therefore, the present invention uses curcumin and various hydrophilic drugs to prepare drug-containing micelles and a second lipophilic drug-containing micelles, and further prepares curcumin-other hydrophilic drug complex pharmaceutical compositions, which are the pharmaceutical compositions capable of being used for localized lipolysis and weight reduction.

The present invention provides a preparation for a curcumin-hydrophilic drug complex pharmaceutical composition, and the curcumin-hydrophilic drug complex pharmaceutical composition comprises drug-containing micelles and a hydrophilic drug; the procedure to prepare the curcumin-hydrophilic drug complex pharmaceutical composition is as follows:

(a5) Mixing curcumin with a solvent and stirring at 150~500 rpm at room temperature until curcumin dissolves completely;

(b5) Adding a pharmaceutically acceptable surfactant and stirring well at 100~300 rpm to volatilize the solvent, wherein, the hydrophilic-lipophilic balance value (HLB value) of the surfactant is greater than 10;

(c5) Once the solvent volatilizes completely, slowly adding a first pharmaceutically acceptable aqueous solution and stirring well at 100~300 rpm to form drug-containing micelles and; and (d5) Filtering through a 0.2 um filter, and storing the filtered solution comprising drug-containing micelles in dark and refrigeration;

Wherein, the first pharmaceutically acceptable aqueous solution comprises a hydrophilic drug.

Preferably, the first pharmaceutical composition comprises a local aesthetic.

Preferably, the local anesthetic is at least one of amides, para-aminobenzoic acid esters, and amino ethers, or combination thereof.

Preferably, the amides are at least one of dibucaine, lidocaine, mepivacaine HCl, bupivacine HCl, pyrrocaine HCl, Prilocaine HCl, digammacaine, and oxethazaine, or combination thereof.

Preferably, the para-aminobenzoic acid esters are at least one of butacaine, dimethocaine, and tutocaine, or combination thereof.

Preferably, the amino ethers are at least one of quinisocaine and pramocaine, or combination thereof.

Preferably, the first pharmaceutically acceptable aqueous solution comprises an antioxidant.

Preferably, the antioxidant is at least one of beta-carotene, lutein, lycopene, bilirubin, vitamin A, vitamin C (ascorbic acid), vitamin E, uric acid, nitric oxide, nitroxide, pyruvate, catalase, superoxide dismutase, glutathione peroxidases, N-acetyl cysteine, and naringenin, or combination thereof.

Preferably, in step (a5), the boiling point of the solvent is lower than that of pure water.

Preferably, in step (a5), the solvent is a hydrophilic solvent.

Preferably, the hydrophilic solvent is at least one of methanol, ethanol, acetone, and other hydrophilic solvents, or combination thereof.

Preferably, the solvent in step (a5) is a lipophilic (hydrophobic) solvent.

Preferably, the lipophilic (hydrophobic) solvent is at least one of ether, benzene, chloroform, dichloromethane, hexane, and other lipophilic (hydrophobic) solvents, or combination thereof.

Preferably, in step (b5), the surfactant is a non-ionic surfactant.

Preferably, the non-ionic surfactant is at least one of polysorbate 80 (TWEEN® 80), polyoxyl 15 hydroxystearate (SOLUTOL® HS 15), polyoxyethylene castor oil derivatives, and other non-ionic surfactants, or combination thereof.

Preferably, the polyoxyethylene castor oil derivative is at least one of KOLLIPHOR® ELP (also known as CREMOPHOR® ELP, polyoxyl 35 castor oil), CREMOPHOR® RH 40 (polyoxyl 40 hydrogenated castor oil), and other polyoxyethylene castor oil derivatives, or combination thereof.

Preferably, between steps (c5) and (d5), it further includes the steps:

(c51) Adding a second pharmaceutically acceptable aqueous solution and mixing well to completely dissolve the second pharmaceutically acceptable aqueous solution.

Preferably, the hydrophilic drug is dissolved in the first pharmaceutically acceptable aqueous solution, the drug-containing micelle is a microstructure formed by the surfactant, and curcumin is encapsulated in said drug-containing micelle.

Preferably, the hydrophilic drug in the first pharmaceutically acceptable aqueous solution is at least one of green tea extract, epigallocatechin gallate, epicatechin, epicatechin gallate, epigallocatechin, gallocatechin gallate, gallocatechin, catechin gallate, catechin, epigallocatechin gallate (EGCG), caffeine, carnitine, L-carnitine, synephrine, chlorogenic acid, and other hydrophilic drugs, or combination thereof.

Preferably, in steps (a5) and (c5), the weight ratio of the curcumin and the hydrophilic drug is 30:1 to 1:10.

Preferably, in steps (a5)~(c5), based on 1 weight unit defined as the total weight of the curcumin and the hydrophilic drug, the weight of the surfactant is 0.24~70 weight units; or, the weight ratio of the total weight of the curcumin and the hydrophilic drug to the surfactant is 4:1 to 1:70.

Preferably, in steps (a5), (c5), and (c51), based on one weight unit defined as the total weight of the curcumin and the hydrophilic drug, the total weight of the first pharmaceutically acceptable aqueous solution and the second pharmaceutically acceptable aqueous solution is 16~400 weight units.

Preferably, in steps (c5) and (c51), the first pharmaceutically acceptable aqueous solution and the second pharmaceutically acceptable aqueous solution are water for injection, aqueous solution for injection, or normal saline.

As demonstrated by the examples of the present invention, the curcumin simple pharmaceutical composition, the curcumin-resveratrol complex pharmaceutical composition, the curcumin-green tea extract complex pharmaceutical composition, the curcumin-other lipophilic drug complex pharmaceutical composition, and the curcumin-hydrophilic drug complex pharmaceutical composition provided by the present invention, and other pharmaceutical compositions provided by the present invention can all reduce the localized fat, and can reduce the body weight. Therefore, the curcumin simple pharmaceutical composition, the curcumin-resveratrol complex pharmaceutical composition, the curcumin-green tea extract complex pharmaceutical composition, the curcumin-other lipophilic drug complex pharmaceutical composition, and the curcumin-hydrophilic drug complex pharmaceutical composition provided by the present invention, and other pharmaceutical compositions provided by the present invention can be used to prepare subcutaneous implanted devices, subcutaneous implants, solutions for implanted infusion, cream, or patches, which is capable of being administered at the sites requiring subcutaneous fat reduction by subcutaneous implantation, implanted infusion, cream, or patch application. Or, the pharmaceutical compositions can be used to prepare subcutaneous implanted devices, subcutaneous implants, solutions for implanted infusion, cream, or patches, which is capable of being administered to an subject by subcutaneous implantation, intravenous injection, implanted infusion, cream, or patch application to reduce the body weight of the subject.

Preferably, the curcumin simple pharmaceutical composition, the curcumin-resveratrol complex pharmaceutical composition, the curcumin-green tea extract complex pharmaceutical composition, the curcumin-other lipophilic drug complex pharmaceutical composition, and the curcumin-hydrophilic drug complex pharmaceutical composition provided by the present invention, and other pharmaceutical compositions provided by the present invention can reduce the fat at the administration site or the body weight by subcutaneous fat injection. Thus, the curcumin simple pharmaceutical composition, the curcumin-resveratrol complex pharmaceutical composition, the curcumin-green tea extract complex pharmaceutical composition, the curcumin-other lipophilic drug complex pharmaceutical composition, and the curcumin-hydrophilic drug complex pharmaceutical composition, and other pharmaceutical compositions provided by the present invention can be used to prepare subcutaneous fat layer injection formulation or subcutaneous injection formulation for reducing localized subcutaneous fat.

Preferably, the curcumin simple pharmaceutical composition, the curcumin-resveratrol complex pharmaceutical composition, the curcumin-green tea extract complex pharmaceutical composition, the curcumin-other lipophilic drug complex pharmaceutical composition, and the curcumin-hydrophilic drug complex pharmaceutical composition provided by the present invention, and other pharmaceutical compositions provided by the present invention can reduce the body weight by subcutaneous fat injection formulation or intravenous injection. Thus, the curcumin simple pharmaceutical composition, the curcumin-resveratrol complex pharmaceutical composition, the curcumin-green tea extract complex pharmaceutical composition, the curcumin-other lipophilic drug complex pharmaceutical composition, and the curcumin-hydrophilic drug complex pharmaceutical composition provided by the present invention, and other pharmaceutical compositions provided by the present invention can be used to prepare subcutaneous fat layer injection formulation, intravenous injection formulation, and subcutaneous injection formulation for reducing body weight.

The foregoing descriptions are merely the preferred embodiments of the present invention and are not intended to limit the scope of patent application of the present invention. Therefore, any alteration or modification that does not depart from the spirits disclosed herein should be included within the scope of patent application of the present invention.

What is claimed is:

1. A pharmaceutical composition, comprising:
   drug-containing micelles; and
   a curcuminoid encapsulated in said drug-containing micelles;
   wherein said drug-containing micelles are a microstructure formed by a first pharmaceutically acceptable polyoxyethylene,
   wherein the hydrophilic-lipophilic balance value (HLB value) of the first polyoxyethylene is greater than 10, and
   wherein the weight ratio of the curcuminoid to the first polyoxyethylene is 1:8 to 1:500.

2. The pharmaceutical composition of claim 1, wherein the first polyoxyethylene is polyoxyl 35 castor oil, polyoxyl 40 hydrogenated castor oil, polyoxyl 15 hydroxystearate, or a combination thereof.

3. The pharmaceutical composition of claim 1, where the curcuminoid is curcumin.

4. The pharmaceutical composition of claim 3, wherein the weight ratio of the curcumin to the first polyoxyethylene is 1:20~1:150.

5. The pharmaceutical composition of claim 1, wherein the concentration of the curcuminoid in the pharmaceutical composition is 0.3~120 mg/g.

6. The pharmaceutical composition of claim 5, wherein the concentration of the curcuminoid in the pharmaceutical composition is 2~91 mg/g.

7. The pharmaceutical composition of claim 1, wherein the diameter of the drug-containing micelles is 3~50 nm.

8. The pharmaceutical composition of claim 7, wherein the diameter of the drug-containing micelles is 5~20 nm.

9. The pharmaceutical composition of claim 1, wherein the pharmaceutical composition further comprises a pharmaceutically acceptable aqueous solution.

10. The pharmaceutical composition of claim 1, wherein the pharmaceutical composition further comprises a second lipophilic drug-containing micelles; wherein the second lipophilic-drug containing micelle is a second microstructure formed by a second polyoxyethylene, and wherein a lipophilic drug is encapsulated in said second drug-containing micelles.

11. The pharmaceutical composition of claim 10, wherein the hydrophilic-lipophilic balance value (HLB value) of the second polyoxyethylene is greater than 10.

12. The pharmaceutical composition of claim 10, wherein the second polyoxyethylene is polyoxyl 35 castor oil, polyoxyl 40 hydrogenated castor oil, polysorbate 80 (tween 80), polyoxyl 15 hydroxystearate, and or a combination thereof.

13. The pharmaceutical composition of claim 10, wherein the lipophilic drug is quercetin, synephrine, puerarin, resveratrol, or a combination thereof.

14. The pharmaceutical composition of claim 10, wherein the weight ratio of the curcuminoid to the lipophilic drug is 30:1~1:10.

15. The pharmaceutical composition of claim 1, wherein the pharmaceutical composition further comprises a hydrophilic drug.

16. The pharmaceutical composition of claim 15, wherein the hydrophilic drug is green tea extract, epigallocatechin gallate, epicatechin, epicatechin gallate, epigallocatechin, gallocatechin gallate, gallocatechin, catechin gallate, catechin, epigallocatechin gallate (EGCG), caffeine, carnitine, L-carnitine, synephrine, chlorogenic acid, or a combination thereof.

17. The pharmaceutical composition of claim 15, wherein the weight ratio of the curcuminoid to the hydrophilic drug is 30:1 to 1:10.

18. The pharmaceutical composition of claim 14, wherein the curcuminoid is curcumin.

19. The pharmaceutical composition of claim 17, wherein the curcuminoid is curcumin.

* * * * *